United States Patent
Wright (10) Patent No.: US 6,177,437 B1
(45) Date of Patent: Jan. 23, 2001

(54) INHIBITORS OF HERPES SIMPLEX VIRUS URACIL-DNA GLYCOSYLASE

(75) Inventor: George E. Wright, Worcester, MA (US)

(73) Assignee: University of Massachusetts Medical Center, Worcester, MA (US)

(*) Notice: Under 35 U.S.C. 154(b), the term of this patent shall be extended for 0 days.

(21) Appl. No.: 09/388,006

(22) Filed: Sep. 1, 1999

Related U.S. Application Data (60) Provisional application No. 60/099,274, filed on Sep. 4, 1998.

(51) Int. Cl.[7] .................... C07D 239/60; C07D 239/54; A61K 31/513; A61K 31/515
(52) U.S. Cl. .................. 514/274; 544/309; 544/310; 544/311; 544/312; 544/314; 544/299; 544/300; 544/301; 544/302
(58) Field of Search ...................................... 544/309, 310, 544/311, 312, 314, 299; 514/274

(56) References Cited

U.S. PATENT DOCUMENTS

| | | | |
|---|---|---|---|
| 5,476,855 | * 12/1995 | Kouni et al. | 514/269 |
| 5,646,155 | 7/1997 | Wright | 514/261 |

OTHER PUBLICATIONS

Argnani, R., et al., "Herpes Simplex Virus Type 1 (HSV-1) Uracil–DNA Glycosylase: Functional Expression in *Escherichia coli*," Biochemical Characterization, and Selective Inhibition by 6–(p–n–Octylanilino) Uracil, *Virology*. 211: 301–311 (1995).
Bowman, C.A., et al., "Asymptomatic herpes simplex virus shedding from the genital tract whilst on suppressive doses of oral acyclovir," *Int. J. STD AIDS* 1: 174–177 (1990).
Focher, F., et al., "Herpes simplex virus type I uracil–DNA glycosylase: isolation and selective inhibition by novel uracil derivatives," *Biochem. J.* 292: 883–889 (1993).
Griffiths, P.D., "A proposal that herpesviruses are co–factors of HIV disease," *Antivir. Chem. Chemother.* 6, (Supp. 1): 17–21 (1995).
Ho, D.Y., "Herpes Simplex Virus Latency: Molecular Aspects," *Prog. Med. Virol.* 39: 76–115 (1992).
Jacobson, J.G., et al., "A herpes simplex virus ribonecleotide reductase deletion mutant is defective for productive acute and reactivatable latent infections of mice and for replication in mouse cells" *Virology* 173: 276–283 (1989).
Jeffries, D.J.; DeClerq, E., Eds. Antiviral Chemotherapy. John Wiley and Sons, Chichester, pp. 199–223 (1995).
Overall, Jr., J.C., "Dermatological Diseases," in Galasso, et al., Antiviral Agents and Viral Diseases of Man, Raven press, New York, pp. 325–384 (1979).

Pregnolato, M., et al., "Synthesis and Molecular Modeling of novel HSV–1 Uracil–DNA glycosylase inhibitors," *Nucleosides & Nucleotides*, 18 (4 & 5), 709–711 (1999).
Price, R.W., "Herpes Simplex Virus Latency: Adaptation to the Peripheral Nervous System. I," *Cancer Invest.* 3: 285–292; II, ibid., 389–403 (1985).
Roizman, B. and Sears, A.E.., "An Inquiry into the Mechanisms of Herpes Simplex Virus Latency," *Annu. Rev. Microbiol.* 41: 543–571 (1987).
Savva, R. et al., "The structural basis of specific base–excision by uracil–DNA glycosylase," *Nature*. 373: 487–493 (1995).
Schwab, I.R. , "Oral Acyclovir in the Management of herpes simplex ocular infections," *Ophthalmology* 95: 423–429 (1988).
Stevens, J.G., et al., "RNA Complementary to a Herpesvirus a Gene mRNA is Prominent in Latently Infected Neurons," *Science* 235: 1056–1059 (1987).
Sun, H., et al., "Molecular Modeling and Synthesis of inhibitors of herpes simplex virus Type 1 Uracil–DNA glycosylase," *J. of Medicinal Chemistry* 42(13): 2344–2350 (1999).
Wildy, P., et al., in Virus Persistence, Mahy, B.W.H., Minson, A.C. and Darby, G.K., eds., Cambridge University Press, Cambridge, pp. 134–167 (1982).
Youle, M.S., et al., "Effects of high–dose oral acyclovir on herpesvirus disease and survival in patients with advanced HIV disease: a double–blind, placebo–controlled study," *AIDS* 8: 641–649 (1994).

* cited by examiner

*Primary Examiner*—John M. Ford
(74) *Attorney, Agent, or Firm*—Lahive & Cockfield, LLP; Peter C. Lauro, Esq.

(57) ABSTRACT

The invention is directed to novel 6-aromatic substituted uracil compounds of formula I

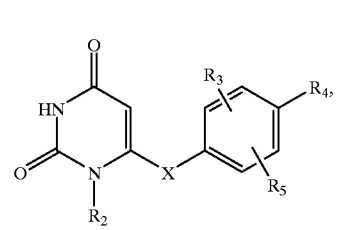

(I)

therapeutic compositions comprising the compounds, and methods of treating Herpes simplex virus Type I and Type II recurrent infections and Herpes simplex virus Type I and Type II encephalitis in humans using the compounds and/or therapeutic compositions.

34 Claims, 1 Drawing Sheet

INHIBITORS OF HERPES SIMPLEX VIRUS URACIL-DNA GLYCOSYLASE

CROSS REFERENCE TO RELATED APPLICATIONS AND INCORPORATION BY REFERENCE

This application claims the benefit of U.S. Provisional Application No. 60/099,274, filed Sep. 4, 1998, which is hereby incorporated by reference in its entirety. All patents, published patent applications and other references cited throughout this specification are hereby incorporated herein by reference in their entireties.

FIELD OF THE INVENTION

The invention relates generally to inhibitors of Herpes Simplex virus uracil-DNA glycosylase (UDG). More particularly, the invention relates to methods of inhibiting the activity of UDG in animals. Still more particularly, the invention relates to novel 6-aromatic substituted uracil compounds, therapeutic compositions thereof, and methods of treating Herpes Simplex virus Type I and Type II recurrent infections and Herpes simplex encephalitis in humans using the compounds and/or therapeutic compositions. All patents, published patent applications and other references disclosed herein are hereby expressly incorporated, in their entirety, by reference.

BACKGROUND OF THE INVENTION

Herpes Simplex virus Type 1 (HSV1), Herpes Simplex virus Type 2 (HSV2). Varcella-Zoster virus (VZV), and Epstein Barr virus (EBV) infections in humans are characterized by episodes of epithelial eruptions involving active virus production alternating with periods without clinical symptoms, i.e., in which the virus is in a latent state. In the case of the herpes virus VZV, the initial acute infection is known as chicken pox, and reactivation from the subsequent latent infection is manifested as the disease shingles. Animal models of the latent state show that at some defined period following inoculation with virus, conventional homogenization techniques are unable to detect free virus, but that the presence of the vital genome can be demonstrated by explanation rescue (cocultivation) techniques (Price, 1985).

In the mouse latency model for HSV1, viral genomes can be detected in sensory ganglia, most abundantly in trigeminal ganglia. The stimuli that cause virus to travel to neural cell bodies, the form of the viral genome present in the cells, and the molecular events that occur during reactivation of the virus are not known.

Herpes simplex virus (HSV), following a primary lytic infection in peripheral mucocutaneous tissues, enters nerve terminals and establishes lifelong latent infections in sensory nerve ganglia (Focher et al., 1993). During latency, no infectious virus is detectable, but such virus can "reactivate" causing recurrent disease at the original site of infection. Typically for HSV1 diseases, latent infection of the trigeminal ganglia is associated with herpes keratitis and infection of cervical ganglia with herpes labialis, whereas for HSV2, latent infections of sacral ganglia are associated with genital infections. Several reviews summarize the understanding of the mechanisms underlying herpes virus latency (Savva et al., 1995; Wildy et al., 1982; Stevens et al., 1987).

Maintenance of the latent state may be mediated by both viral and cellular (host) functions, and may last for the life of the host. Reactivation of the virus may be caused by various environmental, immunological and pharmacological stimuli, and involves replication of the virus genome, centrifugal travel of viral DNA or virus particles through the sensory nerve to the original site of infection, and re-establishment of clinical disease. The morbidity of recurrent herpes virus infections has prompted numerous studies related to treatment or prevention.

Recurrent Herpes simplex infections are significant medical problems. Up to one half of latently infected individuals may have one or more episodes of clinical disease per year. Recurrences are especially serious in immunocompromised patients and with virus strains that are drug resistant. It has even been suggested that herpes viruses are co-factors for HIV disease (Griffiths, 1995). Some AIDS patients experience breakthrough of herpes virus disease even on high dose acyclovir (Youle et al., 1994). Recurrent herpes labialis affects 20–45% of the U.S. population, and about 25% of those have 3 or more recurrences per year (Overall, 1979). Herpes keratitis is the leading cause of blindness in the U.S., and recurrence of this disease in immunocompromised patients has become increasingly associated with morbidity (Schwab, 1988). Recurrent genital herpes is both a medical and a social problem, and, although continuous antiviral treatment is effective, asymptomatic viral shedding can still occur (Bowman et al., 1990).

It is believed that, at present, acyclovir will reduce recurrences in genital infections, but in fact only about 20% of those infected remain recurrence free. In addition, most studies indicate that acyclovir does not prevent viral shedding. Thus, prevention of both recurrent disease and transmissibility to others are important goals in antiviral drug design.

Herpes encephalitis, primarily associated with HSV1, is a disease with high morbidity. Untreated, the mortality rate approaches 90%, and, although acyclovir and araA are effective in reducing mortality, the prognosis for severe cases and the elderly is poor (Jeffries et al., 1995). Antiviral nucleosides may be less effective in encephalitis because of the lack of the activating enzyme, thymidine kinase, in nerve cells.

Development of antiherpetic drugs has focused on targeting inhibitors against the various enzymes encoded by the herpes viruses. Among virus-specific enzymes, the viral DNA polymerase has been an important target for nucleoside analogs such as acyclovir, bromovinyldeoxyuridine and DHPG.

Currently available antiviral drugs such as arabinosyladenine, acyclovir, and phosphonoacetic acid are effective in the treatment of acute HSV infections, but less so in preventing recurrent infections. For example, recurrent herpes labialis and herpes encephalitis in children and older adults are generally resistant to standard antiviral drugs. Acyclovir prevented in vitro reactivation of HSV1 from latently infected trigeminal ganglia of mice only with continuous presence of the drug, as also found for arabinosyladenine and phosphonoacetic acid (Price, 1985). In human patients, the frequency of HSV recurrences following acyclovir treatment were not different than before treatment (Roizman et al., 1987), and it has been suggested that recurrences are longer and more severe in AIDS patients than in immunocompetent patients (Ho, 1992).

HSV1 and HSV2 are known to encode a thymidine kinase ("TK") enzyme in addition to the viral DNA polymerase. The viral DNA polymerase is known to catalyze the replication of the viral genome, although the role(s) of the viral TKs are not well understood. It is thought that herpes virus TK expression is required for the establishment or reactivation of virus from its latent state, particularly in tissues such as peripheral nerve ganglia where host TK expression and DNA synthesis are absent (Price, 1985). Inhibitors of HSV1- and HSV2-TK, and their use for treating recurrent Herpes virus infections are described in U.S. Pat. No. 5,646,155.

Recent results have suggested similar roles for the HSV1-specific uracil DNA glycosylase (UDG) (Jacobson et al., 1989). It is now hypothesized that Herpes Simplex virus Type 1 uracil-DNA glycosylase (HSV-1 UDG or "UDG") is an important enzyme for efficient viral reactivation (Overall, 1979). UDG contributes to post-replicative DNA repair by removal of uracil residues from DNA, resulting either from cytosine deamination or dUTP incorporation, by cleavage of the N-glycosidic bond linking the base to the deoxyribose phosphate backbone. Recent evidence suggests that the viral UDG is required both for virus reactivation from latency and for efficient replication in nerve tissue (Schwab, 1988). The continuous spontaneous deamination of cytosine coupled with the lack of cellular UDG in neurons (Bowman, 1990) are consistent with a requirement for the virus-encoded enzyme in the reactivation and replication of HSV in nerve cells.

OBJECTS OF THE INVENTION

Therefore, it is an object of the invention to provide inhibitors of Herpes Simplex virus uracil-DNA glycosylase (UDG).

It is another object of the invention to provide therapeutic compositions for treatment of recurrent Herpes Simplex infections and herpes simplex encephalitis.

It is yet another object of the invention to provide a method for treating/preventing Herpes Simplex virus recurrent disease in animals, preferably humans.

SUMMARY OF THE INVENTION

In its broadest aspect, the invention is directed to Herpes Simplex virus uracil-DNA glycosylase (UDG), and to methods of inhibiting the activity of UDG in animals. Accordingly, the invention is directed to compounds of formula I (I)

wherein:

X is O NR$_1$, S or CH$_2$;

R$_1$ is hydrogen or (C$_1$–C$_2$)alkyl;

R$_2$ is hydrogen; (C$_2$–C$_6$)alkyl optionally substituted by one or more hydroxyl, amino or carboxyl groups, or by phenyl optionally substituted by (C$_1$–C$_4$)alkyl, carboxyl or amino; (C$_1$–C$_4$)alkoxy(C$_2$–C$_6$)alkyl; N—(C$_1$–C$_4$)alkyl-carboxamido(C$_1$–C$_2$)alkyl; benzyl in which the phenyl moiety is optionally substituted by (C$_1$–C$_4$)alkyl, carboxyl or amino; pyrrolyl(C$_1$–C$_2$)alkyl in which the pyrrole is optionally substituted by (C$_1$–C$_4$)alkyl; or imidazolyl(C$_1$–C$_2$)alkyl in which the imidazole is optionally substituted by (C$_1$–C$_4$)alkyl;

R$_3$ and R$_5$ are the same or different and each is hydrogen; carboxamido; N—(C$_1$–C$_2$)alkylcarboxamido; carboxamidino; or N—(C$_1$–C$_2$)alkylcarboxamidino; and R$_4$ is (C$_6$–C$_{10}$)alkyl optionally substituted by one or more hydroxyl, amino, or carboxyl groups; (C$_6$–C$_{10}$)alkyl where the alkyl moiety can form part of a (C$_4$–C$_8$) cycloalkyl ring; (C$_6$–C$_{10}$)alkenyl; or (C$_1$–C$_{14}$)alkoxy; or a pharmaceutically acceptable salt thereof, with the proviso that when X is NH, R$_3$ and R$_5$ are hydrogen, and R$_4$ is n-propyl, n-butyl, n-pentyl, i-pentyl, n-hexyl or n-octyl, then R$_2$ is not hydrogen.

In one embodiment, the invention is directed to compounds of formula I wherein:

X is O or NH;

R$_2$ is hydrogen; (C$_2$–C$_6$)alkyl optionally substituted by one or more hydroxyl, amino or carboxyl groups, or by phenyl optionally substituted by (C$_1$–C$_4$)alkyl, carboxyl or amino; (C$_1$–C$_4$)alkoxy(C$_2$–C$_6$)alkyl; benzyl in which the phenyl moiety is optionally substituted by (C$_1$–C$_4$)alkyl, carboxyl or amino; pyrrolyl(C$_1$–C$_2$)alkyl in which the pyrrole is optionally substituted by (C$_1$–C$_4$)alkyl; or imidazolyl(C$_1$–C$_2$)alkyl in which the imidazole is optionally substituted by (C$_1$–C$_4$)alkyl;

R$_3$ and R$_5$ are the same or different and each is hydrogen; carboxamido; N—(C$_1$–C$_2$)alkylcarboxamido; carboxamidino; or N—(C$_1$–C$_2$)alkylcarboxamidino; and R$_4$ is (C$_6$–C$_{10}$)alkyl optionally substituted by one or more hydroxyl, amino, or carboxyl groups; (C$_6$–C$_{10}$)alkyl where the alkyl moiety can form part of a (C$_4$–C$_8$) cycloalkyl ring; (C$_6$–C$_{10}$)alkenyl; or (C$_1$–C$_{14}$)alkoxy.

In another embodiment, R$_2$ is HO(CH$_2$)$_n$, HO(C=O)(CH$_2$)$_n$, or H$_2$N(CH$_2$)$_n$, wherein n is 1, 2, 3, 4, or 5, R$_3$ and R$_5$ are hydrogen; and R$_4$ is C$_8$H$_{17}$. Preferably, R$_2$ is CH$_2$CH$_2$OH, CH$_2$CH$_2$CH$_2$OH, CH$_2$CH$_2$NH$_2$, or CH$_2$CH$_2$CH$_2$NH$_2$.

Another embodiment of the invention is directed to compounds of formula I wherein R$_2$ is CH$_3$, C$_2$H$_5$, C$_3$H$_7$, CH$_3$OCH$_2$CH$_2$, CH$_3$OCH$_2$CH$_2$CH$_2$, CH$_2$C(=O)NHCH$_3$, or CH$_2$(C=O)NHCH$_2$CH$_3$.

In yet another embodiment, R$_2$ is CH$_2$Ø-pCH$_3$, CH$_2$Ø-pCO$_2$H, or CH$_2$Ø-mCO$_2$H, wherein the phenyl moiety of the substituents is optionally substituted by (C$_1$–C$_4$)alkyl, carboxyl or amino.

Still another embodiment of the invention is directed to compounds of formula I wherein R$_2$ is 3-isopropyl-2-pyrrolylmethyl, or imidazolylmethyl.

In another embodiment, R$_3$ is C(=O)NH$_2$ or C(=NH)H$_2$, wherein the R$_3$ substituents are ortho to the carbon atom of the phenyl moiety to which the N atom is attached.

In yet another embodiment, R$_4$ is (C$_6$–C$_{10}$)alkyl where the alkyl moiety can form part of a (C$_4$–C$_8$)cycloalkyl ring, or (C$_6$–C$_{10}$)alkenyl. Preferably, R$_4$ is trans, trans-CH=CHCH$_2$CH$_2$CH=CHCH$_2$CH$_3$, or CH$_2$-(trans-1-4-cyclohexyl)-CH$_2$CH$_2$CH$_3$.

Particularly preferred compounds of the invention include:

a) 6-(4-octylphenoxy)uracil;
b) 1-methyl-6-(4-hexylanilino)uracil;
c) 1-ethyl-6-(4-hexylanilino)uracil;
d) 1-propyl-6-(4-hexylanilino)uracil;
e) 1-(2-methoxyethyl-6-(4-hexylanilino)uracil;
f) 1-(3-methoxypropyl)-6-(4-hexylanilino)uracil;
g) 1-(2-hydroxyethyl)-6-(4-hexylanilino)uracil;
h) 1-(3-hydroxypropyl)-6-(4-hexylanilino)uracil;
i) 1-(2-methoxyethyl)-6-(4-octylanilino)uracil;
j) 1-(2-hydroxyethyl)-6-(4-octylanilino)uracil;
k) 6-{4-[trans-(4-propylcyclohexyl)methyl]anilino}uracil;
l) 6-[4-trans, trans-octa-1,5-dienyl)anilino]uracil;
m) 1-(N-methylcarboxamidomethyl)-6-(4-octylanilino) uracil;
n) 1-(N-ethylcarboxamidomethyl)-6-(4-octylanilino)uracil;
o) 1-(4-methylbenzyl)-6-(4-octylanilino)uracil;
p) 1-(4-carboxylbenzyl)-6-(4-octylanilino)uracil;
q) 1-(3-carboxylbenzyl)-6-(4-octylanilino)uracil;
r) 1-(4-isopropyl-2-pyrrolylmethyl)-6-(4-octylanilino) uracil; and
s) 1-(4-isopropyl-2-imidazolylmethyl)-6-(4-octylanilino) uracil.

In another aspect, the invention is directed to therapeutic compositions comprising a therapeutically effective amount of a compound of the invention, or a pharmaceutically acceptable salt thereof, and a pharmaceutically acceptable diluent or carrier. Particularly preferred compositions of the invention comprise compounds a)–s) above. In a preferred embodiment, the compositions are useful for treating Herpes Simplex virus recurrent disease in animals, preferably humans.

In yet another aspect, the invention is directed to a method for treating Herpes simplex virus recurrent disease in animals which comprises administering to an animal in need of said treatment an effective amount of a compound of the invention, or a pharmaceutically acceptable salt thereof, or a pharmaceutical composition comprising either the compound or the salt. The compounds of the invention may be used to prevent or reduce the severity of recurrent HSV1 and HSV2 infections, including infections in non-replicating tissues.

In particular, the methods are provided for using the compounds of the invention for the treatment of herpes virus infections in human patients when the infecting virus encodes a uracil-DNA glycosylase. For example, HSV1, HSV2, VZV, and EBV viral infections causing diseases such as oral herpes, genital herpes, encephalitis, and shingles may be treated. The compounds of the invention are particularly useful for preventing viral reactivation in individuals infected with HSV1, HSV2, VZV, and EBV.

Other features and advantages of the invention will be apparent from the following detailed description and the appended claims.

DETAILED DESCRIPTION OF THE INVENTION

I. Definitions

Certain terms employed in the specification, examples and appended claims are, for convenience, set forth as follows.

The term "alkyl" as used herein generally denotes straight chain, branched chain, or cyclic hydrocarbons, or mixtures thereof, containing 1–10 carbon atoms. Examples of such groups include methyl, ethyl, propyl, isopropyl, n-butyl, isobutyl, tert-butyl, n-heptyl, n-octyl, trans-(4-propylcyclohexyl)methyl, etc.

The term "alkoxy" as used herein denotes an oxygen to which is attached an alkyl moiety as defined above. Examples of alkoxy groups include methoxy, ethoxy, propoxy, n-butoxy, isobutoxy, etc.

The term "alkenyl" generally denotes a straight chain or branched chain hydrocarbon containing 2–10 carbon atoms and one or more double bonds.

The symbol "Ø" is used herein to denote a phenyl moiety which is optionally substituted by one or more groups at the ortho-, meta- and/or para-positions.

The term "animal" as used herein denotes all warm-blooded animals, including mammals, more preferably human beings.

The terms "treatment" and "treating" are used herein in their broadest sense, and include curative and/or prophylactic treatment of Herpes Simplex virus recurrent disease in animals and humans.

The compounds of the invention may contain one or more asymmetric centers and, therefore, can exist as enantiomers or diastereoisomers. Furthermore, certain compounds of the invention containing alkenyl groups may exist as cis-isomers or trans-isomers. In each case, the invention includes both mixtures and separate individual isomers. The compounds may also exist in tautomeric forms and the invention includes both mixtures and separate individual tautomers.

The pharmaceutically acceptable salts of the compounds of the invention which contain a basic center are, for example, non-toxic acid addition salts formed with inorganic acids such as hydrochloric, hydrobromic, sulfuric and phosphoric acid, with organo-carboxylic acids, or with organo-sulphonic acids. Compounds of the invention can also provide pharmaceutically acceptable metal salts, in particular non-toxic alkali metal salts, with bases. Examples include sodium and potassium salts.

II. Therapeutic Administration of Compounds

The compounds of the invention are formulated for pharmaceutical or veterinary use, optionally together with an acceptable diluent, carrier or excipient and/or in unit dosage form. In using the compounds of the invention, conventional pharmaceutical or veterinary practice may be employed to provide suitable formulations or compositions.

Thus, the formulations of this invention can be administered by parenteral administration, for example, intravenous, subcutaneous, intramuscular, intraorbital, opthalmic, intraventricular, intracranial, intracapsular, intraspinal, intracisternal, intraperitoneal, topical, intranasal, aerosol, scarification, and also oral, buccal, rectal or vaginal administration.

The formulations of this invention may also be administered by the use of surgical implants which release the compounds of the invention.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations can be found in, for example, "Remington's Pharmaceutical Sciences." Formulations for parenteral administration may, for example, contain as excipients sterile water or saline, polyalkylene glycols such as polyethylene glycol, oils of vegetable origin, or hydrogenated naphtalenes biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusions systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The compounds of the invention can be used as the sole active agents, or can be used in combination with other active ingredients, e.g., direct antiviral drugs, growth factors which could facilitate neuronal survival in neurological diseases, or peptidase or protease inhibitors.

The concentration of the compound in the formulations of the invention will vary depending upon a number of factors, including the dosage to be administered, and the route of administration. In general terms, the compounds of the invention may be provided in an aqueous physiological buffer solution containing about 0.1 to 10% w/v compound for parenteral administration. General dose ranges are from about 1 mg/kg to about 1 g/kg of body weight per day; a preferred dose range is from about 0.01 mg/kg to 100 mg/kg of body weight per day. The preferred dosage to be administered is likely to depend upon the type and extent of progression of the herpes infection being addressed, the overall health of the patient, and the route of administration. For topical and oral administration, formulations and dosages can be similar to those used for other anti-herpes drugs, e.g. acyclovir.

III. Methods for the Screening of Compounds In Vitro and In Vivo

A. Murine in vitro explant-cocultivation model for HSV1

Screening of compounds is carried out using an in vitro explant cocultivation model in mice. Ocular HSV1 infections are initiated and, after subsidence of the infectious phase (several days), latent HSV1 becomes established in the trigeminal ganglia of the mice. The ganglia are then surgically removed and minced or homogenized, and the explanted tissue is cocultivated on mammalian cells, typically Vero cells. The frequency of reactivation is determined as the percentage of ganglia that produce HSV1 virus (as measured by viral cytopathic effect (CPE)) in the cultures. Effective drugs present during the cocultivation period will decrease the frequency of reactivation relative to untreated cocultures. See (Lelb et al. 1989).

B. Murine eye model for HSV1

About 40–50 days after establishment of latent HSV1 infection (as described above) mice are treated with cyclophosphamide, dexamethasone and ultraviolet irradiation to induce viral reactivation. Eyewashings are taken for inoculation of cultured mammalian cells, typically Vero cells and viral induced CPE is measured. Drugs present during the latency or reactivation phase may decrease the number of animals from which virus can be recovered, or delay the time at which virus appears in the eyewashings. See, (Shimeld et al., 1990), incorporated herein by referenced, for additional experimental detail.

C. Murine ear model for $HSV_1$

After initiation of HSV1 infection of the ears of mice, latent infection becomes established in cervical ganglia. After 3–5 weeks cellophane tape is applied and removed from the ears of mice to induce viral reactivation. Erythema of the ear surface is evidence of reactivation. Drugs present before and/or during the reactivation stimulus may decrease the degree of erythema or relay its onset, and may decrease the yield of virus from explant-cocultivation assays of cervical ganglia. For further experimental methods see, (Hill et al.,1978), incorporated herein by reference.

D. Rabbit and squirrel monkey eye models for HSV1

Several weeks after establishment of latent HSV1 infection in the rabbit eye, sterile deionized water is injected intrastromally to induce reproducible, high frequency reactivation of virus within 48–72 hours. Drug treatment will decrease the numbers of eyes shedding virus, as measured by viral CPE caused by inoculation of cultured mammalian cells with eyewashings, and/or may delay the onset of virus reactivation. See, (Gordon et al., 1990); incorporated herein by reference, for additional experimental detail. An analogous model has been documented in the squirrel monkey, but reactivation occurs spontaneously 25 days or longer after initial infection. See, (Varnell et al., (1987); (Kaufman et al., 1991), all incorporated herein by reference.

E. Guinea pig vaginal model for HSV2

Latent infections of HSV2 become established in dorsal sympathetic ganglia of guinea pigs after vaginal membrane infection. After 48 days animals are observed for recurrent vaginal lesions. Drugs present during the latent phase may decrease the frequency or severity of lesions and/or delay the onset of viral lesions. See, (Stanberry et al.; Bourne et al., 1992), all incorporated herein by reference, for additional experimental detail.

F. Guinea pig model of VZV latency

The most useful animal models of VZV infections or latency involve VZV infection of the cornea of guinea pigs. Guinea pigs are inoculated to cause acute keratitis and the establishment of short term latency in trigeminal ganglia (Pavan-Langston et al., 1989). Latent VZV can be recovered by whole cell coculture from the ganglia 5–11 days following inoculation.

IV. Exemplification

In preliminary investigations, a number of p-alkyl substituted 6-anilinouracils were prepared in accordance with Scheme 1 as follows:

Scheme 1

R
2: C₂H₅
3: C₄H₉-n
4: C₆H₁₃-n
5: C₈H₁₇-n
6: C₁₀H₂₁-n
7: O-C₆H₁₃-n
8: O-C₈H₁₇-n

Reagents: (a) 4-substituted aniline, Δ; (b) sodium 4-n-octylphenate, 2-methoxyethanol.

Reactions of substituted anilines with a 6-chlorouracil in 2-methoxyethanol as solvent (Price et al., 1985; Wright et al., 1980) or without solvent (Baker et al., 1967) are used routinely to prepare 6-anilinouracils in good to moderate yields (Scheme 1). The former method was used to prepare 3-ethyl-6-(4-hexylanilino)uracil and 6-(4-n-decylanilino)uracil 6, while the fusion method was used in the synthesis of 6-(4-n-hexyloxyanilino)uracil 7 and 6-(4'-n-octyloxylanilino)uracil 8. 6-(4-n-Octylphenoxyanilino)uracil 9 was prepared by reacting 6-chlorouracil 1 with sodium p-octylphenolate in 2-methoxyethanol (Scheme 1).

Compounds 2–8 were screened against purified HSV1 and human (HeLa) uracil-DNA glycosylases which were isolated by conventional enzyme purification protocols[1]. Assays for inhibition by the compounds were conducted as described in the literature[1] by measuring [³H]uracil release from [³H]dUMP-containing DNA, in the presence of varying concentrations of test compounds. Control assays contained the same concentration of diluent, dimethylsulfoxide. $IC_{50}$s (the concentration of compound that causes half-maximal inhibition of [³H]uracil release from [³H]dUMP-containing DNA) for each of the compounds were calculated.

The results of the screening program, summarized in Tables 1 and 2 below, revealed that 6-anilinouracils with large n-alkyl groups in the para position of the anilino ring were progressively more potent as inhibitors of the HSV1 enzyme and retained a high degree of selectivity for the viral enzyme (Overall et al., 1979). The most potent compound, 6-(4-n-octylanilino)uracil (octAU) 5, had $IC_{50}=8\,\mu M$ against the viral enzyme but >300 μM against the human enzyme. Compound 5 was competitive with DNA as an inhibitor of HSV1 UDG, in contrast with the reported non-competitive effect of uracil itself as an inhibitor of human UDG (Griffiths (1995). Uracil likely represents a product inhibitor of UDG, whereas the anilinouracils may bind to the enzyme as analogs of the substrate.

Figure 1:
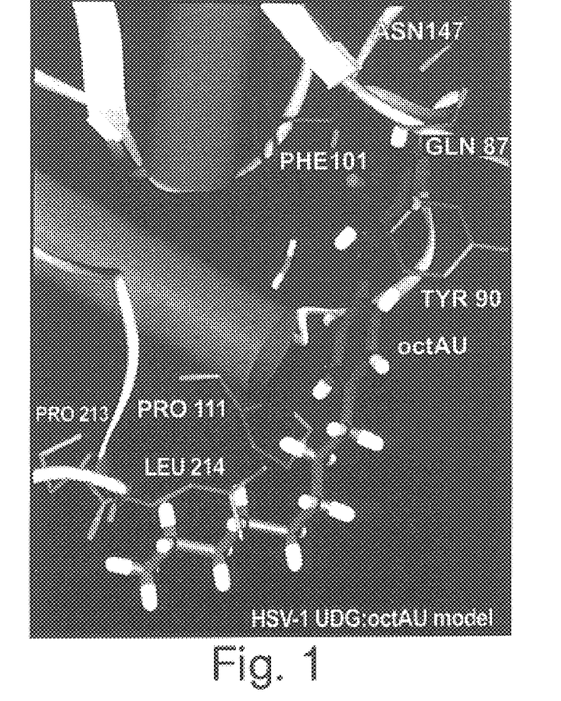
FIG. 1 depicts the molecular structure of the UDG:Uracil complex derived from x-ray crystallography.

As shown in FIG. 1, the x-ray structure of HSV1 UDG complexed with uracil has been determined (Youle et al., 1994). The structure consists of a single domain, with a channeled surface containing a high density of positive charges. Uracil is bound in a pocket in this surface near one end of the protein. Phe 101 forms the floor of the uracil pocket, and Tyr 90 lies perpendicular to and in van der Waals' contact with the uracil 5-H (see detail in FIG. 1). This Tyr residue, the hydrogen bonding of Asn 147 to the 3-NH and 4-oxo groups, and the hydrogen bond from the backbone of Gln 87 explain the uracil specificity of the enzyme. The uracil 1-NH is hydrogen bonded to a water molecule which is at the mouth of the binding pocket. A second complex between HSV1 UDG and $(dT)_3$ shows the hydrophobic sugar and base 5-methyl backbone of the trinucleotide lining a hydrophobic cleft at the mouth of the uracil pocket (Youle et al., 1994).

It is believed that these inhibitors bind to HSV1 UDG in the uracil binding site. A molecular modeling study with the coordinates of the uracil:UDG structure was undertaken to determine a plausible model for the binding affinity and selectivity of 6-(p-alkylanilino)uracils for HSV1 UDG (FIG. 1). The structure and activity of the new hydrophilic derivatives disclosed below were predicted based on the model.

Modeling and Structural Design

From the preliminary investigations described above, compound 5,6-(4-n-Octylanilino)uracil ("octAU"), was selected as the lead compound because it demonstrated the best inhibition of the viral enzyme, although structural modifications in order to increase the binding affinity and to improve physicochemical properties such as water solubility were indicated. For further drug development, structural information about octAU:UDG interaction was desirable for rational lead optimization, but attempts to grow octAU:UDG co-crystals failed partly due to the poor water solubility of the inhibitor (Jeffries et al., 1995).

Consequently, a structure-based rational design approach, starting with computer-assisted prediction of the inhibitor binding mode in the enzyme-inhibitor complex, was undertaken. The calculations and simulations were performed on an Indigo 2 R10000 SGI workstation, by using the software modules Discover, Biopolymer, Dock and LUDI in the Biosym/MSI package.

OctAU 5 is a highly flexible molecule with ten freely rotatable single bonds, and it can adopt many low energy conformations in solution. The real situation in docking the inhibitors to the enzyme becomes more complex if the flexibility of the enzyme is taken into account. To make docking feasible, two strategies, the "ligand build-up" and the "in-site combinatorial search" were applied (Klein et al., 1981).

The coordinates of HSV-1 UDG in complex with uracil (Youle et al., 1994) consist of 1928 heavy atoms. Hydrogen atoms were added automatically using the Builder module with the value of pH set to the physiological value of 7.4. The resulting system had a net charge of −7.0. To remove any artifacts introduced by adding explicit hydrogen atoms, the structure was subjected to steepest descents (sd) minimization for 500 iterations with all backbone atoms tethered. After removing all the water molecules except two at the active site, which are believed to be related to enzymatic function, the structure was further minimized for 1,000 steps using the sd algorithm to relax any remaining hot spots. The backbone atoms of the resulting structure had a root mean square (rms) deviation of 0.20 Å from the crystal coordinates.

The 6-anilinouracil (AU) molecule was built up in the protein by attaching an anilino group to the uracil C-6. If the uracil is assumed to stay in its original position, the AU molecule has only two degrees of freedom, representing a suitable case for in-site combinatorial search. By rotating the two dihedral angles around C-6/N ($\phi$) and N/C-1' (in the phenyl ring) ($\psi$) while monitoring the change of the intermolecular interaction energy, the local conformational space was efficiently sampled. Favorable interactions were achieved only when $\phi$ was about 150°. Because the variation of the angle $\psi$ will not affect the position of C-4' in the phenyl ring, where the octyl group is attached, $\psi$ was arbitrarily set to 150°. The n-octyl group was then added in two carbon units, with energy minimization after each addition. For each minimization procedure, those amino acids 12 Å away from the binding site were fixed, and the remaining amino acids and the uracil ring were tethered to their original positions by a template force of 100.0 kcal/Å for 100 cycles. The template force was gradually released in another 100 steps, followed by 200 cycles of sd minimization without any external forces. The rms deviation was only 0.28 Å upon superimposing the backbone atoms of the enzyme before and after docking with compound 5. The final structure was fully minimized using the sd method until the maximum derivative was less than 0.5 kcal/Å, and by the method of conjugate gradients until the maximum derivative was less than 0.01 kcal/Å.

Figure 2:
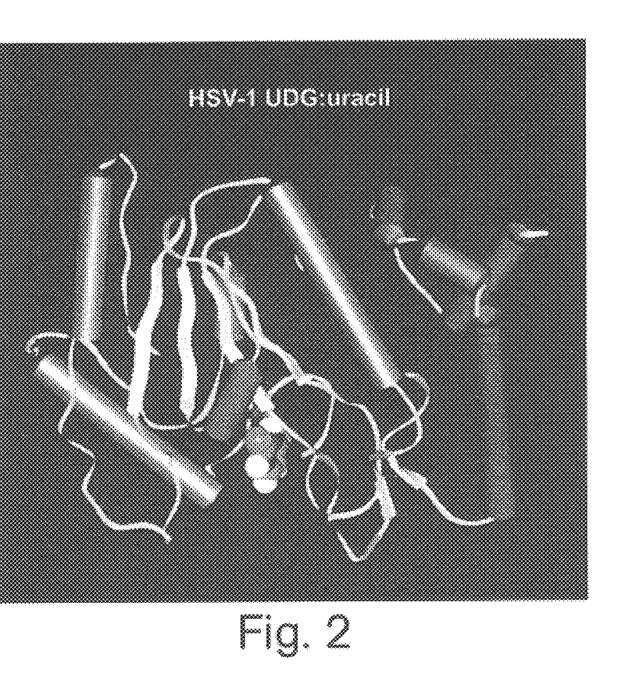
FIG. 2 depicts a computer-generated model of the energy minimized structure of the UDG:6-(4-n-Octlyanilino)uracil.

The structural model of octAU:UDG resulting from the energy minimization procedure is shown in FIG. 2. The model shows that the uracil ring of the inhibitor binds in the same position as free uracil in the UDG crystal structure. The 6-NH bond is approximately perpendicular to the phenyl ring of Tyr 90 at a distance of 3.85 Å, an interaction energetically equivalent to about half of a normal hydrogen bond. The second half of the octyl chain lies snugly in a hydrophobic cleft on the surface of the enzyme formed by the side chains of Pro 111, Pro 213, and Leu 214. The hydrophobic side chains of leucines and prolines are typically buried in the interior of proteins, but the appearance of Pro 111, Pro 213, and Leu 214 on the surface of UDG is required by the biological function of the protein. In the case of the human UDG structure (Mattison et al., 1988), the counterpart of Leu 214 was proposed to insert into the DNA through the minor groove assisting flipping of the nucleotide to be removed, and he Leu-DNA interactions stabilized the extrahelical nucleotide conformation. Comparison between the calculated complex structure in FIG. 2 and the crystal structure of HSV1 UDG bound to trithymidylate (Youle et al., 1994) revealed similar interactions, although the two ligands are very different. By superimposing the backbone atoms of the enzymes (rms=0.71 Å), a similar orientation of 5 and the first two thymidylates of the trimmer was observed.

In the crystal structure the first thymine remains at the mouth of the uracil binding pocket because of steric hindrance, and the second thymine base packs against the hydrophobic sidechains of Pro 213 and Leu 214, and its attached deoxyribose ring packs against the side chain of Pro 111, the latter believed to be one of the major driving forces for ligand binding. The hydrophobic interactions are quite similar to those found in the modeled octAU:UDG complex (FIG. 1). Hydrophobic effects play a pivotal role in many chemical phenomena in aqueous solution (Pyles et al., 1994), and the association of the hydrophobic n-octyl group with the similarly hydrophobic residues on the surface of the protein may play the central role in inhibitor binding in this case. Molecular recognition relies strongly on non-covalent interactions, for which hydrophobic regions in host and guest are often crucial.

Correlation of Activity with Model Based Energy Calculations

Table 1 summarizes the intermolecular interaction energies ($E_{inter}$) between HSV-1UDG and alkylanilinouracils obtained during the ligand buildup procedure described above. The results are separated into van der Waal's and coulombic components. It is clear that a direct relation exists between the total energies and $IC_{50}$ values of the inhibitors, as emphasized by the correlation equation between $pIC_{50}$[−log($IC_{50}$)] and total energy for the series of compounds:

$$pIC_{50} = -0.23565 E_{inter} - 6.5588 (n=4, R^2=0.987)$$

TABLE 1

Molecule-molecule interaction energy summary for alkylanilinouracils.

| Ligand | Total Energy (kcal/mole) | van der Waals' (kcal/mole) repulsion − dispersion = total | | | Coulombic (kcal/mole) | $IC_{50}$[a] ($\mu$M) |
|---|---|---|---|---|---|---|
| 2 | −41.78024 | 44.2178 | 69.8937 | −25.67595 | −16.10429 | 500 |
| 3 | −44.44710 | 44.0705 | 73.7932 | −29.72274 | −14.72436 | 150 |
| 4 | −46.52708 | 46.3444 | 78.1175 | −31.77312 | −14.75397 | 30 |
| 5 | −49.03306 | 51.4240 | 85.0409 | −33.61688 | −15.41618 | 8 |

[a]From (Youle, 1994)

Using this equation, the activities of novel inhibitors before synthesis were predicted. Table 2 summarizes the calculated interaction energies and comparison of predicted and observed $IC_{50}$ values for compounds 6–9. The structure of 6-(4-n-decylanilino)uracil 6 was built by adding two methylene groups to the alkyl chain of octAU. The binding modes of 6-(4-n-hexyloxyanilino)uracil 7 and 6-(4-n-octyloxyanilino)uracil 8 were generated from 5 and 6, respectively, by replacing the corresponding atoms and deleting the unnecessary atoms, followed by energy minimization. The above equation was used to predict $IC_{50}$ values from the total interaction energies derived from energy minimization of each inhibitor:UDG model.

Compounds 6–9 were synthesized and assayed for their inhibitory potencies against HSV1 UDG. The predicted $IC_{50}$ values are in good agreement with the experimental ones, being on the same order although lower than experimental $IC_{50}$s by 2–3-fold (Table 2). These differences may result in part from underestimating the dehydration energy of the free ligands. These results serve both to validate the model of inhibitor:enzyme interaction and to permit prediction of the activity of new inhibitors.

TABLE 2

Summary of molecule-molecule interaction energies, and calculated and experimental $IC_{50}$ values of novel inhibitors.

| Ligand | Total Energy (kcal/mole) | Van der Waals' (kcal/mole) Repulsion-dispersion = total | | | Coulombic (kcal/mole) | $IC_{50}^a$ (μM) | $IC_{50}^b$ (μM) |
|---|---|---|---|---|---|---|---|
| 6 | −48.70344 | 50.1479 | 84.2068 | −34.05885 | −14.64459 | 12 | 35 |
| 7 | −48.13001 | 50.6867 | 83.5828 | −32.89606 | −15.23395 | 16 | 30 |
| 8 | −49.00301 | 51.3359 | 85.4334 | −34.09749 | −14.90552 | 10 | 25 |
| 9 | −45.01171 | 53.5577 | 87.9681 | −34.41046 | −10.60125 | 89 | 150 |

[a]Predicted value.
[b]Experimental value.

Derivatization of Alkylanilinouracils

According to the inhibitor model of FIG. 1, substituents at N-3 or at C-5 of the uracil ring were expected lead to lack of inhibition. Indeed, 3-ethyl-6-(4-n-hexylanilino)uracil and the 5-methyl "thymine" analog (4-n-hexylanilino)thymine were inactive at 200 μM against viral UDG, although the parent compound 4 had $IC_{50}$ of 30 μM.[11] Substitution of the 3-NH not only blocks the hydrogen bond to Asn 147, but would produce steric clash with this residue. Substitution at C-5 similarly would produce steric clash with the ring of Tyr 90. One site on the uracil ring where substituents may be tolerated is N-1. In the x-ray structure, a water molecule is hydrogen bonded to 1-NH, and a volume that could be filled with substituents of moderate size is available in the dehydrated enzyme.

1-Substituted-6-anilinouracils

Accordingly, several derivatives of 6-aminouracil and of a 6-alkylanilinouracil with hydrophilic 1-substituents were prepared in accordance with Scheme 2 below. 6-Aminouracil itself has been reported to inhibit weakly human UDG (Caradonna et al, 1981), and, indeed, the recent x-ray structure of the human enzyme was solved in the presence of this compound (Mole et al., 1995). 6-(4-n-Hexylanilino)uracil was chosen as the platform inhibitor for these syntheses for the simple reason of economy, 4-hexylaniline being considerably less expensive than 4-octylaniline.

1-Alkyl-6-aminouracils were made in one step from the corresponding alkylurea

| n | $R_1$ | | R |
|---|---|---|---|
| 21: 2 | $C_6H_{13}$ | 11,16: | $CH_3$ |
| 22: 3 | $C_6H_{13}$ | 12,17: | $C_2H_5$ |
| 25: 2 | $C_8H_{17}$ | 13,18: | $C_3H_7$ |
| | | 14,19: | $CH_3OCH_2CH_2$ |
| | | 15,20: | $CH_3OCH_2CH_2CH_2$ |
| | | 24: | $CH_3OCH_2CH_2$ |

Reagents:
(a) NC—$CH_2$—COOEt, NaEtOH
(b) P-hexylanilin, p-hexylanilin hydrochloride,
(c) TMSI/$CHCl_3$ and ethyl cyanoacetate (Traube, 1990; Biltz et al., 1925) (Scheme 2). N-Substituted ureas 10 were cyclized with ethyl cyanoacetate in ethanol in the presence of sodium ethoxide, to give 1-substituted-6-aminouracils 11–15.

Activated amino groups in pyrimidines are readily displaced by nucleophiles, including both aliphatic and aromatic amines (Whitehead et al, 1960; Goldner et al., 1966). For oxoamino pyrimidines, e.g. cytosine and 1,3-dimethyl-6-aminouracil, Whitehead and Traverso found that heating with amines to 160–170° C. without solvent required an equivalent of the amine hydrochloride to give the substitution product. This reaction was used to prepare 1-alkyl-6-(4-n-hexylanilino)uracils 16–18 (Scheme 2). The synthesis of 1-(2-hydroxyethyl)-6-(4-n-hexylanilino)uracil 21 was attempted by the fusion reaction starting from 1-(2-hydroxyethyl)-6-aminouracil. However, considerable decomposition occurred under the high temperatures required for this reaction. Therefore, the methoxy-protected 6-aminouracils 14–15 were successfully constructed by fusion reactions to give the corresponding 1-(2-methoxyethyl)- and 1-(3-methoxypropyl)-6-(4-n-hexylanilino)uracils, 19 and 20, respectively. Demethylation of the ethers with trimethylsilyl iodide (Jung et al., 1977) afforded the expected 1-(2-hydroxyethyl) and 1-(3-hydroxypropyl)-6-(4-n-hexylanilino)uracils 21 and 22, respectively. A similar sequence was used to prepare the analogous 1-(2-methoxyethyl)- and 1-(2-hydroxyethyl)-6-(4-n-octylanilino)uracils, 24 and 25, respectively, in good yields.

Compounds were assayed as described above, and the results are summarized in Table 3.

TABLE 3

Effect of compounds on HSV1 and human uracil-DNA glycosylases

| Compound | Substituent | IC$_{50}$ ($\mu$M) HSV1-UDG | Human-UDG |
|---|---|---|---|
| 6-substituted uracils | 6-substituent | | |
| 5[a] | NH-C$_6$H$_4$-p-C$_8$H$_{17}$ | 8 | >300 |
| 6 | NH-C$_6$H$_4$-p-C$_{10}$H$_{21}$ | 35 | >200 |
| 7 | NH-C$_6$H$_4$-p-OC$_6$H$_{13}$ | 30 | — |
| 8 | NH-C$_6$H$_4$-p-OC$_8$H$_{17}$ | 25 | — |
| 9 | O-C$_6$H$_4$-p-C$_8$H$_{17}$ | 150 | >300 |
| 1-substituted-hexAU | 1-substituent | | |
| 4a | H | 30 | >300 |
| 16 | CH$_3$ | c | >200 |
| 17 | C$_2$H$_5$ | c | >200 |
| 18 | C$_3$H$_7$ | c | >200 |
| 19 | CH$_2$CH$_2$OCH$_3$ | >100 | — |
| 20 | CH$_2$CH$_2$CH$_2$OCH$_3$ | >100 | — |
| 21 | CH$_2$CH$_2$OH | 20 | — |
| 22 | CH$_2$CH$_2$CH$_2$OH | 90 | — |
| 1-substituted-octAU | | | |
| 24 | CH$_2$CH$_2$OCH$_3$ | 15 | — |
| 25 | CH$_2$CH$_2$OH | 10 | — |

[a]From (Focher et al., 1993).
[b]These data are not available as IC$_{50}$.

6-Aminouracil was a weak inhibitor of HSV1 UDG with IC$_{50}$=1 mM. As shown in Table 3, 1-alkyl-6-aminouracils 11–13 also weakly inhibited the viral enzyme, but were not significantly more potent than the parent compound. The analogous 1-alkyl hexAU derivatives 16–18 were, unfortunately, too insoluble in assay medium to estimate inhibition potencies. Only 10–15% inhibition of HSV1 UDG activity was observed with these compounds at 40 $\mu$M.

The 1-(2-hydroxyethyl) derivative 21 was equipotent with 4, although the 1-(3-hydroxypropyl) derivative 22 was 3-fold weaker. The corresponding methoxyalkyl compounds were weaker still (Table 3). Although the introduction of hydrophilic 1-substituents did not result in increased potency of the platform inhibitor, the compounds had apparent increased water solubility and maintained, at least for the small 2-hydroxyethyl group, similar inhibitory activity. Encouraged by the results with hexAU we synthesized and assayed the corresponding octAU derivatives (Table 3). Indeed, 1-(2-hydroxyethyl)octAU 25 was as a potent an inhibitor as 5, and the 1-(2-methyoxyethyl) compound 24 was nearly as potent.

These results provide further support for the model of inhibitor:UDG binding presented above, and validate the strategy, described below, for developing more water soluble derivatives. In particular the potential use of a compound such as 25 to test the role of HSV 1 UDG expression in viral reactivation becomes more feasible, given the likely improved absorption and distribution of this derivative in appropriate animal models. The same strategy applied to a different family of inhibitors of HSV1 thymidine kinase (TK) (Xu et al., 1995) another viral enzyme implicated in the reactivation process, did result in demonstration of efficacy to reduce the frequency of HSV1 recurrences in two animal models (Gephardt et al, 1996; Kaufman et al., 1996).

Synthesis of Hydrophilic Derivatives

To obtain UDG inhibitors with increased water solubility, a series of 1-($\omega$-methoxyalkyl)- and 1-($\omega$-hydroxyalkyl)-6-(4-n-octylanilino)uracils are prepared in accordance with Scheme 2. Other hydrophilic 1-substituents are introduced by methods known in the art.

To prepare true water soluble compounds, the hydroxyalkyl compounds can be converted to the corresponding aminoalkyl derivatives by the sequence of Scheme 3 below (Hata et al., 1975). Salts, e.g., hydrochlorides, of these compounds are conveniently prepared. In accordance with Scheme 3, the 1-(2-aminoethyl) and 1-(4-aminobutyl) derivatives are prepared.

Scheme 3

Synthesis of Model-Based Inhibitors

Using the optimized model of octAU:UDG binding (FIG. 2), three compounds were selected for synthesis based on the predicted interaction energy with UDG as compared to octAU. As shown in Table 4, an increase of about 9 kcal/mole for each compound is predicted for the interaction energy compared with octAU.

TABLE 4

Predicted interaction energies (kcal/mol) of new octAU derivatives with HSV1 UDG

| Ligand | van der Waals' | Coulombic | Total |
|---|---|---|---|
| octAU | −45.98 | −14.66 | −60.60 |
| 1-carboxymethyl-octAU | −51.65 | −18.08 | −69.70 |
| 2'-carboxamido-octAU | −51.05 | −18.36 | −69.40 |
| 2'-carboxamidino-octAU | −52.07 | −18.16 | −70.20 |

In the cases of the 2'-substituted compounds, the new substituent may potentially interact with a nearby Asp 88. These compounds are prepared as follows.

1-Carboxymethyl-octAU. This compound is prepared by the general method outlined in Scheme 2. Cyclization of carboxymethylurea with ethyl cyanoacetate gives 1-carboxymethyl-6-aminouracil. Fusion with p-octylaniline and its hydrochloride gives 1-carboxymethyl-octAU. Alternately, carboxymethylation of 2-methylmercapto-6-(p-octylanilino)-4-pyrimidone, separation of the 1-isomer, and hydrolysis of the 2-methylmercapto or 2-methylsulfone gives this compound. (The latter sequence has been carried out successfully to prepare the 1-acetoxyethyl derivative of hexAU.)

2'-Carboxamido and 2'-carboxamidino-octAUs. Preparation of a common aniline precursor, 2-cyano-4-octylaniline, is required for these compounds(Scheme 4). p-Octylaniline is acylated to either the acetamide or isobutyramide to protect the amino group. The protecting group must be stable during subsequent acidic conditions, but be readily removable after the cyano group is introduced. Both the acetamido (Khorana et al., 1961) and isobutyramido groups (Büchli et al., 1972) are acid stable, and can be removed by mild alkaline hydrolysis. Nitration by standard conditions gives 2-nitro-4-octylacetanilide or isobutyranilide. Catalytic reduction to the amino derivative is followed by diazotization and cyanation via the Sandmeyer reaction (e.g. Org. Syn. Coll. Vol. I, 514) to give the 2-cyano-4-octyl amide.

Following hydrolysis, the aniline is reacted with 6-chlorouracil to give 6-(2-cyano-4-octylanilino)uracil as shown in Scheme 5. Although the aniline is both hindered and deactivated, the literature (Wright et al., 1980; Medveczky et al., 1995) suggests that the anilinouracil can be prepared in the usual way from 6-chlorouracil. Finally, peroxide-catalyzed hydration (e.g. Org. Syn. Coll. Vol. II, 44, 586) affords 2'-carboxamido-octAU, and amination with ammonium chloride/ammonia (Schaefer et al., 1962) gives 2'-carboxamidino-octAU as the hydrochloride.

Other 1-Substituted Derivatives

Several additional 1-substituents were predicted to increase affinity of octAU for the UDG binding site:

e f g

It is unlikely that carbonylpyrimidines containing fragments c–f will be stable. Accordingly, the analogous methylene isosteres are prepared and introduced in the octAU molecule.

A second synthetic strategy is to manipulate the p-octyl group of octAU. One series of predictions involves introducing hydroxyl groups at specific positions in the octyl chain to take advantage of possible hydrogen bonding to Ser 212, close to C3 of the octyl chain in the model. The specific compound predicted to have increased affinity is 6-[4-(5-hydroxyoctyl]-anilinouracil. Another series involves decreasing the flexibility of the octyl group by introducing the cyclohexane ring or double bonds at specific places. Two specific compounds are predicted to closely overlap the octyl group conformation in the UDG:octAU model: 6-{4-[trans-(4-propylcyclohexyl)-methyl]anilino}uracil and 6-[4-(trans,trans-octa-1,5-dienyl)anilino]uracil. These two compounds are prepared by known methods as set forth in Scheme 1.

Biochemical and In Vitro Assays a. Isolation and assay of uracil-DNA glycosylases. The viral and human (HeLa) uracil-DNA glycosylases are isolated with conventional enzyme purification protocols (Focher et al., 1993). Both long and short forms of the HSV1 enzyme have been cloned and expressed in *E. Coli* (Argnani et al., 1995), and have essentially identical enzymatic properties and inhibitor sensitivities. Assays for new inhibitors of viral and human UDG are done as described (Focher et al., 1993) by measuring [$^3$H]uracil release from [$^3$H]dUMP-DNA. Mechanism studies involve classical variable substrate assays to determine if inhibition is competitive with substrate or product.

b. Antiviral and cytotoxicity testing. Compounds are submitted to the antiviral evaluation program at NIAID for screening against herpes virus growth in cell cultures and for cytotoxicity in uninfected cells. Results of these assays provide levels of activity against HSV1, HSV2, VZV, HCMV (human cytomegalovirus) and EBV (Epstein-Barr virus) in culture, and cytotoxicity against host cells. Further animal testing of compounds that show substantial cytotoxicity in these assays, i.e., $IC_{50}$s that are tenfold or less than their antiUDG $IC_{50}$s, is discontinued.

Dosing and Pharmacokinetics in Animals a. Solubility. Water solubility is measured spectrophotometrically for saturated aqueous solutions of compounds at 25° C. as described (Xu et al., 1995). Partition coefficients between 1-octanol and water are determined with saturated solutions of compound in water or isotonic buffered saline, pH 7.4, partitioned with 1-octanol. Concentrations in the two phases are measured spectrophotometrically as described (Xu et al., 1995). Both the absolute aqueous solubility and the partition coefficient ($\gamma=C_o/C_w$) are used to correlate with pharmacokinetic parameters (see below).

b. Dosage formulations. Compounds having suitable potency against HSV1 UDG and significant water solubility are formulated into pharmaceutical compositions suitable for use in treating animals by the intraperitoneal, intravenous and oral routes of administration. Such formulations are dependent upon the physicochemical properties of the specific compound. The following formulations are developed: 1) solutions in saline at pH as close to 7.4 as possible; 2) solutions in 90% dimethylsulfoxide in saline; 3) solutions in corn oil; 4) suspensions in saline at pH 7.4, and 5) suspensions in corn oil. The feasibility of dosing animals by dissolving compound(s) in drinking water and measuring water consumption to ascertain the exact dose received is determined. The latter method has been used for long term dosing of mice with acyclovir (Klein and Czelusniak, 1990).

c. Analytical methods. High performance liquid chromatography (HPLC) conditions are developed for determining plasma and tissue concentrations of compounds in mice. Considering that the physicochemical properties of new uracil derivatives may differ from those of TK inhibitors previously studied (Xu et al., 1995), those HPLC conditions are modified. For these studies, a C8 reverse phase column with an eluting solvent consisting of a mixture of water and acetonitrile containing 0.2% acetic acid is used to elute the compounds in regions free from plasma or tissue constituents. Blood samples are centrifuged, and the plasma passed through Sep-pak columns prior to HPLC analysis. Tissue samples are homogenized in phosphate buffered saline, and the homogenates are centrifuged and treated as for plasma. Detection of the eluates is done with a variable wavelength uv detector tuned to the $\lambda_{max}$ of the compound. The lower limit of measurement of compounds in undiluted plasma will be about 0.5–1 $\mu$M (Xu et al., 1995).

For the study of compounds, alterations in solvent composition, the use of water:methanol mixtures as eluting solvent, or the use of C18 columns for more polar compounds, are explored to find optimal conditions for candidate drugs. Because desired minimum drug concentrations are in the 1–10 micromolar range, the HPLC method should be of adequate sensitivity for the initial evaluation of the compounds.

d. Pharmacokinetics and tissue distribution. Candidate compounds for antiviral testing should exhibit a high bioavailability (i.e. be well absorbed following oral or parenteral administration), a large volume of distribution (be widely distributed among tissues), and a long half-life (be persistent in plasma), while at the same time being relatively non-toxic.

Single doses of compound are administered to mice by the intraperitoneal, oral and/or intravenous route, and blood is collected after decapitation at predetermined times after treatment in order to characterize the time course of the resultant levels of drug in plasma. The data are used to estimate the apparent volume of distribution of the compound, as an indirect measure of tissue distribution, and the plasma half life, as an indicator of rate of elimination (Xu et al., 1995). Dependence of these parameters on vehicle and route of administration guides development of dosing schedules for antiviral testing.

Methods for the analysis of tissue levels of promising compounds are developed. The partitioning of the compounds into major organs/tissues is examined, especially into whole brain and those tissues that harbor latent herpes viruses, like the peripheral nervous supplies of the eyes and reproductive organs. However, the small size of the latter tissues may preclude determining their content of an unlabelled compound. In such cases, levels in brain are used as a predictor: if a drug enters the whole brain it would certainly be expected to enter the peripheral neuronal structures.

4. Toxicity Studies a. Acute toxicity. Compounds are tested to determine the acute (24 hr) lethality of single intraperitoneal doses of compound, as determined by administration of progressively increasing doses of compounds to groups of four mice each. Subsequently, that formulation and one or more of the other formulations are administered to groups of four or more mice each by the intravenous and oral routes (either by gavage or in drinking water). After treatment, all animals are monitored for signs of toxicity. Animals that become moribund or exhibit severe toxicity are sacrificed by decapitation. Otherwise, one-half of the animals are sacrificed at 24 hr after treatment and the remaining animals at 7 days after treatment. All animals are subjected to a careful gross necropsy with particular attention to the injection/treatment site(s). Any major organs or tissues that are abnormal in size or appearance are fixed in Formalin for microscopic examination.

b. Chronic toxicity. Chronic toxicity is determined for compounds that are candidates for detailed antiviral studies in mice. Repeated dose experiments in which, depending on the pharmacokinetic properties of the compounds, mice are treated one or more times daily for up to 21 days, are conducted on three groups of ten mice each. One group is treated with the maximum tolerated dose of the compound, determined from the acute toxicity experiments, one group with one third of this dose, and one group with the vehicle alone. Signs of general and organ toxicity resulting from each compound are monitored as described above.

Treatment Schedules for In Vivo Antiviral Testing

Where selected compounds are to be administered to animals in order to assess antiviral activity in vivo, the ability of such animals to tolerate the proposed treatment schedules is determined in a separate series of experiments using animals of the same species, sex and age. Also, the plasma, serum and, perhaps, tissue levels associated with such treatments are determined, to assure that the antiviral testing employs optimal treatment schedules, thereby minimizing the possibility of false negative conclusions about in vivo anti-reactivation and antiviral activity.

Tests for Reactivation of HSV1 from Latency in Animals

The murine in vitro explant-cocultivation model for HSV1 reactivation allows preliminary assessment of inhibitors of reactivation (e.g. see Leib et al., 1990). Murine eye (Shimeld et al., 1990) and ear (Hill et al., 1978) models for HSV1 reactivation, rabbit (Gordon et al., 1990) and squirrel monkey (Kaufman et al., 1991) eye models for HSV1 reactivation, and a guinea pig vaginal model for HSV2 reactivation (Stanberry et al., 1982) are available for in vivo testing.

Experiments to determine efficacy of the compounds are performed. Two in vivo models of HSV1 latency may be used for this purpose, the murine eye model of heat stressed reactivation, and the squirrel monkey model of cold stressed reactivation. Both models have been used to demonstrate efficacy of TK inhibitors (Gebhardt et al., 1996; Kaufman et al., 1996). HSV2 reactivation in the guinea pig vaginal model is also conducted.

Vertebrate Animals

1. Use of mice. Experiments are conducted in unanesthetized mice to describe toxic effects of single and repeated doses of compounds, and to describe the pharmacokinetic properties of the same substances.

a. Selection of doses. The toxicities of single doses of compounds are determined in groups of four animals each. When the drug is to be given intraperitoneally and orally by gavage, progressively larger doses are given until a dose is found that gives toxicity. The doses selected for study vary by a factor of about three, using the following schedule: 1, 3, 10, 30, 100 etc. mg/Kg. If the compound is given orally in drinking water, the concentration of the compound in the water is increased in successive groups of animals, also by a factor of about three, and the water consumption per group of animals will be measured, and the average dose in mg/Kg per animal is calculated.

b. Necropsies. When or if animals die as a result of compound treatment, and when animals are sacrificed for any reason, they are necropsied. The internal body surfaces and the linings and contents of the abdominal and thoracic cavities are examined visually for organs or tissues of abnormal size and appearance. Abnormal organs and/or pieces of abnormal-appearing tissues are saved in Formalin. When animals have received repeated daily doses of a compound, the following major organs are examined, weighed and saved in Formalin whether or not they appear abnormal: brain, heart, lung, liver, spleen, pancreas, adrenals, kidney and testes. These tissues will be available for microscopic examination if deemed desirable at a future date.

c. Blood and tissue samples. Blood samples are obtained from mice after decapitation by simply collecting the blood draining from the body in heparinized tubes. In cases where sensitive methods have been developed for analysis of the compound in plasma, blood can be collected from periorbital veins via a capillary tube, a widely used and accepted method of obtaining blood from mice. Tissue samples are obtained from mice after decapitation in order to determine the potential of compounds to partition in selected organs or tissues.

2. Justification. One or more animal models of viral diseases are used to evaluate selected compounds as antiviral agents in humans. The bulk of such studies are conducted in mice because mice are used widely for animal models of herpes virus diseases. Where species-related differences in toxicity and pharmacokinetics are present studies in guinea pigs, rabbits and/or squirrel monkeys are conducted on the most promising of the compounds found effective in mice.

Compounds are selected for detailed study, including the conduct of repeated-dose experiments in which animals are treated one or more times daily for up to 21 days. These experiments utilize three groups each of ten animals—one group is treated with a dose that might be considered the maximum tolerated dose, one group with one-third this dose and one group with the vehicle.

Chemical Synthesis

Melting points were measured using a Mel-temp hot-stage apparatus and are uncorrected. $^1$H nmr spectra were recorded at 300 MHz using a Varian Unity 300 spectrometer. $^1$H chemical shifts (δ) are reported with Me$_4$Si (δ=0.00 ppm) as internal standard. The following abbreviations are used: s=singlet, d=doublet, t=triplet and m=multiplet. Elemental Analyses were within ±0.4% of the theoretical values and were performed on a Carlo Erba 1106 Elemental Anal.yser. All reactions were monitored by TLC on 0.25 mm Merck silica gel (60 F254) visualized by UV light (λ=264 or 365 nm). Flash chromatography was performed using silica gel (60–200 μm, Merck). Compounds 2–5 were prepared as previously reported (Price, 1995). 3-Ethyl-6-(p-hexylanilino)uracil was prepared by standard methods, isolated in 38% yield (from toluene), mp 235°. Anal. (C$_{18}$H$_{25}$N$_3$O$_2$) C,H,N. 6-(4-Hexylanilino)thymine was prepared by reaction of 6-aminothymine with the aniline, and was isolated in 35% yield (from toluene), mp 247–248°. Anal. (C$_{17}$H$_{23}$N$_3$O$_2$)) C,H,N.

6-(4-Decylanilino)uracil, 6. A mixture of 6-chlorouracil (146.5 mg, 1.0 mmol) and 4-decylaniline (467 mg, 2.0 mmol) was placed in a pear-shaped flask and heated to 200° C. for 2 h under nitrogen. The greenish reaction mixture was washed with 15 mL of chloroform and then crystallized from AcOH/H$_2$O, giving 310 mg (90%) of white crystals, mp 292–293° C. $^1$H NMR (DMSO-d$_6$): δ=2.55 (t, 2H, ArCH$_2$), 4.60 (s, 1H, 5-H, 7.15 (2d, 4H, C$_6$H$_4$), 8.14 (s, 1H, 6-NH), 10.13 (s, 1H, 1-NH), 10.43 (s, 1H, 3NH). Anal. (C$_{20}$H$_{29}$N$_3$O$_2$) C, H, N.

6-(4-Hexyloxyanilino)uracil, 7. A mixture 6-chlorouracil (146.5 mg, 1.0 mmol) and 4-n-hexyloxyaniline (2.0 mmol) was heated at 200° C. in a oil bath for 3 h under nitrogen. The cooled mixture was washed with 25 mL, of 1:1 EtOH/H$_2$O and then crystallized from AcOH/H$_2$O giving 300 mg (95%) of purple crystals, mp 320° C. $^1$H NMR (DMSO-d$_6$): δ=3.95 (t, 2H, OCH$_2$), 4.41 (s, 1H, 5-H), 6.92 and 7.10 (2d, 4H, C$_6$H$_4$), 7.96 (s, 1H, 6-NH), 10.13 (s, 1H, 1-NH), 10.37 (s, 1H, 3-NH). Anal. (C$_{16}$H$_{21}$N$_3$O$_3$) C, H, N.

6-(4-Octyloxyanilino)uracil, 8. This product was prepared by the same procedure described above except that 4-n-octyloxyaniline (7.0 mmol) was employed. Crystallization from AcOH/H$_2$O gave grey crystals (95%), mp 318° C. $^1$H NMR (DMSO-d$_6$): δ=3.95 (t, 2H, OCH$_2$), 4.41 (s, 1H, 5-H), 6.80 and 7.07 (2d, 4H, C$_6$H$_4$), 8.02 (s, 1H, 6-NH), 12.80 (s, 1H, 3-NH). Anal. (C$_{18}$H$_{25}$N$_3$O$_3$), C, H, N.

6-(4-Octylphenoxy)uracil, 9. A mixture of 6-chlorouracil (146.5 mg, 1.0 mmol) and sodium p-octylphenate (206 mg, 1.0 mmol) was heated to 125° C. in a oil-bath for 2 h under nitrogen. The reaction mixture was washed with 10 mL of EtOH and then crystallized from AcOH/H$_2$O, giving 90 mg (30%) of white crystals, mp 212–215° C. $^1$H-NMR: δ0.89 (t 3H, CH$_3$), 1.30 (m, 8H, CH$_2$) (m, 2H, Ar—CH$_2$—CH$_2$), 2.60 (t, 2H, Ar—CH$_2$—CH$_2$), 4.19 (s, 1H, H-5), 7.18 and 7.30 (d, 4H), 10.95 (s, 1H, NH), 11.87 (s, 1H, 3-NH) Anal. (C$_{18}$H$_{24}$N$_2$O$_3$) C, H, N.

1-Alkyl-6-aminouracils, 11–15. Sodium ethoxide was prepared from sodium (200 mmol) and 150 mL of "super-dry" EtOH. The corresponding alkylurea (100 mmol) and ethyl cyanoacetate (100 mmol) were added and the mixture was refluxed for 6 h. The mixture was concentrated to half volume and chilled on ice for 1 h. The product was collected by filtration. Recrystallization from H$_2$O (pH=7.0) gave over 90% yield of 1-alkyl-6-aminouracil. 1-Methyl-6-aminouracil, 11. Yield 95%; mp 310–312° C.; $^1$H-NMR: δ3.17 (s 3H, CH$_3$), 4.54 (s, 1H, H-5), 6.75 (s, 1H, NH), 10.29 (s, 1H, 3-NH). Anal. (C$_5$H$_7$N$_3$O$_2$) C, H, N. 1-Ethyl-6-aminouracil, 12. Yield 95%; mp 297–298° C.; $^1$H-NMR: δ1.08 (t, 3H, CH$_3$), 3.77 (q, 2H, CH$_2$), 4.52 (s, 1H, H-5), 6.79 (s, 1H, NH), 10.29 (s, 1H, 3-NH). Anal. (C$_6$H$_9$N$_3$O$_2$) C, H, N. 1-Propyl-6-aminouracil, 13. Yield 96%; mp 279–281° C.; $^1$H-NMR: δ0.85 (t, 3H, CH$_3$), 1.51 (m, 2H, CH$_2$), 3.67 (t, 2H, CH$_2$), 4.51 (s, 1H, H-5), 6.78 (s, 1H, NH), 10.30 (s, 1H, 3-NH). Anal. (C$_7$H$_{11}$N$_3$O$_2$) C, H, N.

1-Alkyl-6-(4-hexylanilino)uracils, 16–20. To a mixture of 1-alkyl-6-aminouracil (10 mmol) and 4-hexylaniline hydrochloride, a few drops of 4-hexylaniline were added to wet the solid. Under the protection of nitrogen, the mixture was heated at 165° C. for 6 h in an oil bath. The reaction mixture was washed with 20 mL of 1:1 EtOH/H$_2$O, filtered and the solid crystallized from AcOH/H$_2$O. 1-Methyl-6-(4-hexylanilino)uracil, 16. Yield 85%; mp 268° C. $^1$H-NMR: δ3.37 (s 3H, CH$_3$), 4.43 (s, 1H, H-5), 8.41 (s, 1H, NH), 10.61 (s, 1H, 3-NH). Anal. (C$_{17}$H$_{23}$N$_3$O$_2$) C, H, N. 1-Ethyl-6-(4-hexylanilino)uracil, 17. Yield 95%; mp 222–225° C. $^1$H-NMR: δ1.18 (t, 3H, CH$_3$), 3.99 (q, 2H, CH$_2$), 4.33 (s, 1H, H-5), 8.43 (s, 1H, NH), 10.60 (s, 1H, 3-NH). Anal. (C$_{18}$H$_{25}$N$_3$O$_2$) C, H, N. 1-Propyl-6-(4-hexylanilino)uracil, 18. Yield 96%; mp 226° C. $^1$H-NMR: δ0.85 (t, 3H, CH$_3$), 1.61 (m, 2H, CH$_2$), 3.89 (t, 2H, CH$_2$), 4.31 (s, 1H, H-5), 8.41 (s, 1H, NH), 10.60 (s, 1H, 3-NH). Anal. (C$_{19}$H$_{26}$N$_3$O$_2$) C, H, N.

(2-Methoxyethyl)urea was synthesized employing 2-methoxyethylamine and potassium cyanate in H$_2$O as described previously. Colorless needles were obtained (94% yield), mp 74–76° C. $^1$H NMR (DMSO-d$_6$): δ3.11 (m, 2 H, CH$_2$N), 3.24 (s, 3 H, CH$_3$O), 3.31(t, 2 H, CH$_2$O), 5.45 (s, 2 H, NH$_2$) and 5.95 (s, 1 H, NH) ppm.

(3-Methoxypropyl)urea 3-Methoxypropylurea was prepared by the same procedure as above. $^{34,35}$ Colorless needles were obtained (90% yield), mp 76–78° C. $^1$H NMR (DMSO-d$_6$): δ1.57 (m, 2 H, CH$_2$), 2.98 (m, 2 H, CH$_2$N), 3.21 (s, 3 H, CH$_3$O), 3.31 (t, 2 H, CH$_2$O), 5.39 (s, 2 H, NH$_2$) and 5.92 (s, 1H, NH) ppm.

1-(2-Methoxyethyl)-6-aminouracil, 14. Sodium methoxide was prepared from sodium (4.0 g, 174 mmol) and 100 mL of anhydrous MeOH. (2-Methoxyethyl)urea (6.0 g, 50.8 mmol) and ethyl cyanoacetate (5.75 g, 50.8 mmol) were added, and the mixture was refluxed for 6 h. The mixture was allowed to cool, and 2 N HCl was added until the solution was weakly acidic. The inorganic salts were removed by filtration on a short column filled with silica gel. The solvent was removed in vacuo, and 7.7 g of 14 (82% yield) was obtained as a grey solid. Crystallization from EtOH/H$_2$O gave white crystals, mp 236–238° C. $^1$H NMR (DMSO-d$_6$): δ3.26 (s, 3 H, CH$_3$O), 3.46 (t, 2 H, CH$_2$N), 3.95 (t, 2 H, CH$_2$O), 4.55 (s, 1 H, C$_5$—H), 6.66 (s, 2 H, NH$_2$) and 10.35 (s, 1 H, NH) ppm. Anal. (C$_7$H$_{11}$N$_3$O$_3$) C, H, N.

1-(3-Methoxypropyl)-6-aminouracil, 15. This compound was prepared by the same procedure as above. Yield: 86%. Crystallization from EtOH gave white crystals, mp 209.5–211° C. $^1$H NMR (DMSO-d$_6$): δ1.72 (m, 2 H, CH$_2$), 3.21 (s, 3 H, CH$_3$O), 3.36 (t, 2 H, CH$_2$N), 3.77 (t, 2 H, CH$_2$O), 4.52 (s, 1 H, C$_5$—H), 6.73 (s, 2 H, NH$_2$) and 10.30 (s,1 H, NH) ppm. Anal. (C$_8$H$_{13}$N$_3$O$_3$) C, H, N.

1-(2-Methoxyethyl)-6-(4-hexylanilino)uracil, 19. A mixture of 14 (0.2 g, 1.1 mmol), 4-hexylaniline hydrochloride (0.26 g, 1.2 mmol) and a few drops of 4-hexylaniline was heated at 160° C. for 40 min. After cooling to room temperature, the product was chromatographed on silica gel with chloroform:methanol (97:3–95:5) as eluent, to give 0.32 g (86% yield) of 19. Crystallization from EtOH/H$_2$O gave white crystals, mp 188–190° C. $^1$H NMR (DMSO-d$_6$): δ3.34 (s, 3 H, CH$_3$O), 3.59 (t, 2 H, CH$_2$N), 4.16 (t, 2 H, CH$_2$O), 4.47 (s, 1 H, C$_5$—H), 7.17 (dd, 4 H, Ar—H), 8.26 (s, 1 H, NH) and 10.68 (s, 1 H, NH) ppm. Anal. (C$_{19}$H$_{27}$N$_3$O$_3$) C, H, N.

1-(3-Methoxypropyl)-6-(4-hexylanilino)uracil, 20. This compound was prepared by the same procedure as above for 19. Yield: 85%. Crystallization from EtOH/H$_2$O gave white crystals, mp 112–113° C. $^1$H NMR (DMSO-d$_6$): δ0.85 (m, 3 H, CH$_3$), 1.28 (m, 6 H, 3×CH$_2$), 1.57 (m, 2 H, CH$_2$), 1.85 (m, 2 H, CH$_2$), 2.58 (t, 2 H, CH$_2$Ar), 3.23 (s, 3 H, CH$_3$O), 3.40 (t, 2 H, CH$_2$N), 4.00 (t, 2 H, CH$_2$O), 4.36 (s, 1 H, C$_5$—H), 7.19 (dd, 4 H, Ar—H), 8.36 (s, 1 H, NH) and 10.61 (s, 1 H, NH) ppm. Anal. (C$_{20}$H$_{29}$N$_3$O$_3$) C, H, N.

1-(2-Hydroxyethyl)-6-(4-hexylanilino)uracil, 21. Iodotrimethylsilane (0.25 mL, 1.76 mmol) was added to a stirred solution of 19 (173 mg, 0.5 mmol) in dry CHCl$_3$ (15 mL). The reaction mixture was stirred at room temperature until disappearance of the starting material (tlc, about 4h). MeOH (10 mL) and 0.5 g sodium sulfite were then added to the brown-purple solution. After stirring at room temperature for 30 min., the mixture was filtered and the solvent was removed. The residue was purified by chromatography on silica gel with CHCl$_3$/MeOH (90:10) as eluent, to give 146 mg (88% yield) of 21. Crystallization from EtOH/H$_2$O gave white crystals, mp 245–247° C. $^1$H NMR (DMSO-d$_6$): δ0.85 (m, 3 H, CH$_3$), 1.28 (m, 6 H, 3×CH$_2$), 1.57 (m, 2 H, CH$_2$), 2.57 (t, 2 H, CH$_2$Ar), 3.67 (t, 2 H, CH$_2$N), 4.05 (t, 2 H, CH$_2$O), 4.55 (s, 1 H, C$_5$—H), 5.62 (br, 1 H, OH), 7.15 (dd, 4 H, Ar—H), 8.50 (br, 1 H, NH) and 10.70 (s, 1 H, NH) ppm. Anal. (C$_{18}$H$_{25}$N$_3$O$_3$) C, H, N.

1-(3-Hydroxypropyl)-6-(4-hexylanilino)uracil, 22. Iodotrimethylsilane (0.2 mL, 1.41 mmol) was added to a stirred solution of 20 (108 mg, 0.3 mmol) in dry CHCl$_3$ (10 mL). The reaction mixture was stirred for 4 h at room temperature. MeOH (10 mL) and 0.5 g sodium sulfite were then added to the brown-purple solution. After stirring at room temperature for 30 min., the mixture was filtered and the solvent was removed. The residue was purified by chromatography on silica gel with CHCl$_3$/MeOH (97:3–90:10) as eluent, to give 32 mg (30% yield) of starting material, 56 mg (54% yield) of 22, and 8 mg (8% yield) of compound 23 (see below). Crystallization of 22 from EtOH/H$_2$O gave white crystals, mp 173–175° C. $^1$H NMR (DMSO-d$_6$): δ0.86 (m, 3 H, CH$_3$), 1.28 (m, 6 H, 3×CH$_2$), 1.57 (m, 2 H, CH$_2$), 1.79 (m, 2 H, CH$_2$), 2.58 (t, 2 H, CH$_2$Ar), 3.50 (t, 2 H, CH$_2$N), 3.98 (t, 2 H, CH$_2$O), 4.41 (s, 1H, C$_5$—H), 5.00 (br, 1 H, OH), 7.19 (dd, 4 H, Ar—H), 8.52 (br, 1 H, NH) and 10.65 (s, 1 H, NH) ppm. Anal. (C$_{19}$H$_{27}$N$_3$O$_3$) C, H, N.

N$^1$, N$^6$-Propylene-6-(4-hexylanilino)uracil, 23. Iodotrimethylsilane (0.2 ml, 1.41 mmol) was added to a stirred solution of 20 (108 mg, 0.3 mmol) in CHCl$_3$ (10 mL). The reaction mixture was stirred at room temperature until disappearance of the starting material 20 (about 14 h). MeOH (10 mL) and 0.5 g sodium sulfite were then added to the brown-purple solution. After stirring at room temperature for 30 min., the mixture was filtered and the solvent was removed. The residue was purified by chromatography on silica gel with CHCl$_3$/MeOH (97:3) as eluent, to give 81 mg (82%) of 23. Crystallization from EtOH/H$_2$O gave white crystals, mp>220° C. $^1$H NMR (DMSO-d$_6$): δ0.86 (m, 3 H, CH$_3$), 1.29 (m, 6 H, 3×CH$_2$), 1.58 (m, 2 H, CH$_2$), 2.10 (m, 2 H, CH$_2$), 261 (t,2 H, CH$_2$Ar), 3.55 (t, 2 H, CH$_2$N), 3.83 (m, 3 H, CH$_2$O and C$_5$—H), 7.29 (dd, 4 H, Ar—H) and 10.51 (s, 1 H, NH) ppm. Anal. (C$_{19}$H$_{25}$N$_3$O$_2$) C, H, N.

1-(2-Methoxyethyl)-6-(4-octylanilino)uracil, 24. A mixture of 14 (0.6 g, 3.24 mmol), 4-octylaniline hydrochloride (0.78 g, 3.24 mmol) and a few drops of 4-octylaniline (0.74 ml, 3.24 mmol) was heated at 160° C. for 40 min under nitrogen. After cooling to room temperature, the product was chromatographed on silica gel with CHCl$_3$/MeOH (97:3) as eluent, to give 1.02 g (85% yield) of 24. Crystallization from EtOH/H$_2$O gave white crystals, mp 189–193° C. $^1$H NMR (DMSO-d$_6$): 3.38 (s, 3 H, CH$_3$O), 3.60 (t, 2 H, CH$_2$N), 4.15 (t, 2 H, CH$_2$O), 4.49 (s, 1 H, C$_5$—H), 7.18 (dd, 4 H, Ar—H), 8.25 (s, 1 H, NH) and 10.68 (s, 1 H, NH) ppm. Anal. (C$_{21}$H$_{31}$N$_3$O$_3$) C, H, N.

1-(2-Hydroxyethyl)-6-(4-octylanilino)uracil, 25. Iodotrimethylsilane (1.1 mL, 7.7 mmol) was added to a stirred solution of 24 (720 mg, 1.93 mmol) in dry CHCl$_3$ (20 mL). The reaction mixture was stirred at room temperature until disappearance of the starting material (tlc, about 12 h). MeOH (25 mL) and sodium sulfite were then added to the brown-purple solution until the color almost disappeared. After stirring at room temperature for 30 min., the mixture was filtered and the solvent was removed. The residue was purified by chromatography on silica gel with CHCl$_3$/MeOH (90:10) as eluent, to give 550 mg (79% yield) of 25. Recrystallization from EtOH/H$_2$O gave white crystals, mp 241–245° C. $^1$H NMR (DMSO-d$_6$): δ0.90 (m, 3 H, CH$_3$), 1.30 (m, 10 H, 5×CH$_2$), 1.57 (m, 2 H, CH$_2$), 2.60 (t, 2 H, CH$_2$Ar), 3.68 (t, 2 H, CH$_2$N), 405 (t, 2H, CH$_2$O). 4.55 (s, 1 H, C$_5$—H), 5.62 (br, 1 H, OH), 7.15 (dd, 4 H, Ar—H), 8.50 (br, 1 H, NH) and 10.66 (s, 1 H, NH) ppm. Anal. (C$_{20}$H$_{29}$N$_3$O$_3$) C, H, N.

Elemental Analyses

3-Ethyl-6-(4-hexylanilino)uracil Calcd. for C$_{18}$H$_{25}$N$_3$O$_2$: C, 68.57; H, 7.94; N, 13.33. Found: C, 68.54; H, 7.87; N, 13.30.

6-(4-Hexylanilino)thymine Calcd. for C$_{17}$H$_{23}$N$_3$O$_2$: C, 67.77; H, 7.64; N, 13.95. Found: C, 67.84; H, 7.83; N, 13.89.

6-(4-Decylanilino)uracil, 6. Calcd. for C$_{20}$H$_{29}$N$_3$O$_2$: C, 69.94; H, 8.51; N, 12.23. Found: C, 70.43; H, 8.89; N, 11.47.

6-(4-Hexyloxyanilino)uracil, 7. Calcd. for C$_{16}$H$_{21}$N$_3$O$_3$: C, 63.35; H, 6.98; N, 13.85. Found: C, 63.53; H, 7.08; N, 13.46.

6-(4-Octyloxyanilino)uracil, 8. Calcd. for C$_{18}$H$_{25}$N$_3$O$_3$: C, 65.23; H, 7.60; N, 12.68. Found: C, 65.31; H, 7.93; N, 13.02.

6-(4-Octylphenoxy)uracil, 9. Calcd. for C$_{18}$H$_{24}$N$_2$O$_3$: C, 68.33; H, 7.65; N, 8.85. Found: C, 68.65; H, 7.70; N, 8.60.

1-Methyl-6-aminouracil, 11. Anal. Calcd. for C$_5$H$_7$N$_3$O$_2$: C,; H,; N,. Found: C,; H,; N,.

1-Ethyl-6-aminouracil, 12. Anal. Calcd. for C$_6$H$_9$N$_3$O$_2$: C,; H,; N,. Found: C,; H,; N,.

1-Propyl-6-aminouracil, 13. Anal. Calcd. for C$_7$H$_{11}$N$_3$O$_2$: C,; H,; N,. Found: C,; H,; N,.

1-Methyl-6-(4-hexylanilino)uracil, 16. Calcd. for C$_{17}$H$_{23}$N$_3$O$_2$: C, 67.75; H, 7.69; N, 13.94. Found: C, 67.55; H, 7.86; N, 14.08.

1-Ethyl-6-(4-hexylanilino)uracil, 17. Calcd. for C$_{18}$H$_{25}$N$_3$O$_2$: C, 68.54; H, 7.99; N, 13.32. Found: C, 68.34; H, 8.28; N, 12.98.

1-Propyl-6-(4-hexylanilino)uracil, 18. Calcd. for C$_{19}$H$_{26}$N$_3$O$_2$: C, 69.48; H, 7.98; N, 12.79. Found: C, 69.14; H, 8.31; N, 12.50.

1-(2-Methoxyethyl)-6-aminouracil, 14. Calcd. for C$_7$H$_{11}$N$_3$O$_3$: C, 45.40; H, 5.99; N, 22 69. Found: C, 45.33; H, 6.29; N, 22.70.

1-(3-Methoxypropyl)-6-aminouracil, 15. Calcd. for C$_8$H$_{13}$N$_3$O$_3$: C, 48.24; H, 6.58; N, 21.09. Found: C, 48.09; H, 6.68; N, 21.14.

1-(2-Methoxyethyl-6-(4-hexylanilino)uracil, 19. Calcd. for C$_{19}$H$_{27}$N$_3$O$_3$: C, 66.06; H, 7.88; N, 12.16. Found: C, 65.96; H, 8.07; N, 12.13.

1-(3-Methoxypropyl)-6-(4-hexylanilino)uracil, 20. Calcd. for C$_{20}$H$_{29}$N$_3$O$_3$: C, 66.83; H, 8.13; N, 11.69. Found: C, 66.64; H, 7.74; N, 11.89.

1-(2-Hydroxyethyl)-6-(4-hexylanilino)uracil, 21. Calcd. for $C_{18}H_{25}N_3O_3$: C, 65.23; H, 7.60; N, 12.68. Found: C, 64.90; H, 7.93; N, 12.63.

1-(3-Hydroxypropyl)-6-(4-hexylanilino)uracil, 22. Calcd. for $C_{19}H_{27}N_3O_3$: C, 66.06; H, 7.88; N, 12.16. Found: C, 65.83; H, 7.68; N, 12.49.

$N^1$, $N_6$-Propylene-$N_6$-(4-hexylphenyl)aminouracil, 23. Calcd. for $C_{19}H_{25}N_3O_2$: C, 69.70; H, 7.70; N, 12.83. Found: C, 69.71 ; H, 7.77 ; N, 12.94.

1-(2-Methoxyethyl)-6-(4-octylanilino)uracil, 24. Calcd. for $C_{21}H_{31}N_3O_3$: C, 67.53; H, 8.37; N, 11.25 Found: C, 67.53; H, 8.37; N, 11.25.

1-(2-Hydroxyethyl)-6-(4-octylanilino)uracil, 25. Calcd. for $C_{20}H_{29}N_3O_3$: C, 66.82; H, 8.13; N, 11.69. Found: C, 66.74; H, 8.21; N, 11.64.

References (1) Price, R. W. (1985) Herpes Simplex Virus Latency: Adaptation to the Peripheral Nervous System. I, Cancer Invest. 3: 285–292; II, ibid., 389–403.

(2) Focher, F.; Verri, A.; Spadari, S.; Manservigi, R.; Gambino, J.; Wright, G. E. (1993) Herpes simplex virus type I uracil-DNA glycosylase: isolation and selective inhibition by novel uracil derivatives. Biochem. J. 292: 883–889.

(3) Savva, R.; McAuley-Hecht, K.; Brown, T.; Pearl, L. (1995) The structural basis of specific base-excision by uracil-DNA glycosylase. Nature. 373, 487–493.

(4) Wildy, P.; Field, H. J.; Nash, A. A. (1982) in Virus Persistence, Mahy, B. W. H., Minson, A. C. and Darby, G. K., eds., Cambridge University Press, Cambridge, pp. 134–167.

(5) Stevens, J. G.; Wagner, E. K.; Devi-Rao, G.; Cook, M. L.; Feldman, L. (1987) RNA Complementary to a Herpesvirus a Gene mRNA is Prominent in Latently Infected Neurons. Science 235: 1056–1059.

(6) Griffiths, P. D. (1995) Antivir. Chem. Chemother. 6, (Supp. 1): 17–21.

(7) Youle, M. S.; Gazzard, B. G.; Johnson, M. A.; Cooper, D. A.; Hoy, J. F.; Busch, H.; Rif, B.; Griffiths, P. D. Stephenson, S. L.; Dancox, M. (1994) Effects of high-dose oral aciclovir on herpesvirus disease and survival in patients with advanced HIV disease: a double-blind, placebo-controlled study. AIDS 8: 641–649.

(8) Overall, Jr., J. C. (1979) "Dermatological Diseases," in Galasso, et al., Antiviral Agents and Viral Diseases of Man. Raven Press, New York, 1979, pp 325–384.

(9) Schwab, I. R. (1988) Ophthalmology 95: 423–429.

(10) Bowman, C. A.; Wooley, P. D.; Herman, S. (1990) Int. J. STD AIDS 1: 174–177.

(11) Jeffries, D. J.; DeClerq, E., Eds. (1995) Antiviral Chemotherapy. John Wiley and Sons, Chichester, pp 199–223.

(12) Roizman, B.; Sears, A. E. (1987) An Inquiry into the Mechanisms of Herpes Simplex Virus Latency. Annu. Rev. Microbiol. 41: 543–571.

(13) Ho, D. Y. (1992) Herpes Simplex Virus Latency: Molecular Aspects. Prog. Med. Virol. 39: 76–115.

(14) Jacobson, J. G.; Leib, D. A.; Goldstein, D. J.; Bogard, C. L. Schaffer, P. A.; Weller, S. K.; Coen, D. M. (1989) Virology 173: 276–283.

(15) Lelb (1989) J. Virol. 63:759–768

(16) Shimeld, C.; Hill, T. J.; Blyth, W. A.; Easty, D. L. (1990) J. gen. Virol. 71: 397–404.

(17) Hill, T. J.; Blyth, W. A.; Harbour, D. A. (1978) J. gen. Virol. 39: 21–28.

(18) Gordon (1990), Invest. Ophthalmol. Vis. Sci. 31:921–924

(19) Varnell (1987), Curr. Eye Res. 6:277–279

(20) Kaufman, H. E.; Varnell, E. D.; Cheng, Y. C.; Bobek, M.; Thompson, H. W.; Dutschman, G. E. (1991) Antiviral Res. 16: 227–232.

(21) Stanberry (1992), J. Infect. Dis. 146:397–404

(22) Bourne (1992), Antimicr. Agents Chemother. 36:2020–2024

(23) (Pavann-Langston, D. and Dunkel, E. C. (1989), Arch. Ophathalmol. 107, 1068–1072

(24) Wright, G. E.; Brown, N. C. (1980) Inhibitors of Bacillus Subtilis DNA Polymerase III. 6-Anilinouracils and 6-(Alkylamino)uracils. J. Med. Chem. 23: 34–38.

(25) Baker, B. R.; Rzeszotarski, W. (1967) Irreversible Enzyme Inhibitors CIV. Inhibitors of Thymidine Phosphorylase VIII. Further Studies on Hydrophobic Bonding with 6-Substituted Uracils. J. Med. Chem. 10: 1109–1113.

(26) Klein, R. J.; DeStefano, E.; Friedman-Kien, A. E.; Brady, E. (1981) Effect of acyclovir on latent herpes simplex virus infections in trigeminal ganglia of mice. Antimicrob Agents Chemother. 19 (5): 937–939.

(27) Mattison, H. R.; Reichman, R. C.; Benedetti, J.; Bolgiano, D.; Davis, L. G.; Bailey-Farchione, A.; Remingon, M.; Winter, C.; Corey, L. (1988) Double-blind, placebo-controlled trial comparing long term suppressive therapy with short term oral acyclovir therapy for the management of recurrent genital herpes. Am. J. Med. Suppl. 2A 85: 20–25.

(28) Pyles, R. B.; Thompson, R. L,. (1994) Evidence that the Herpes Simplex Virus Type 1 Uracil DNA Glycosylase Is Required for Efficient Viral Replication and Latency in the Murine Nervous System. J. Virol. 68: 4963–4972.

(29) Traube, W. (1900) Der synthetische Aufbau der Harnsäure, des Xanthins, Theobromins, Theophyllins und Caffeins aus der Cyanessigsäure. Ber. 33: 3035–3056.

(30) Biltz, H; Peukert, E. (1925) 3-Äthyl-harnsäure und 3-Athyl-xanthin. Chem. Ber. 58: 2190–2199.

(31) Whitehead, C. W.; Traverso, J. J. (1960) Exchange Amination. Alkyl and Arylamino-pyrimidines and Purines. J. Am. Chem. Soc. 82: 3971–3974.

(32) Goldner (33) Jung, M. E.; Lyster, M. A.; (1977) J. Org. Chem., 42, 3761

(34) Hata, 1975)

(35) Büchli, H.; Khorana, H. G. (1972) J. Mol. Biol. 72: 251–288.

(36) Khorana, H. G.; Turner, A. F.; Vizsolyi, J. P. (1961) J. Am. Chem. Soc. 83: 687–698.

(37) Medveczky, M.; Yang, T.-F.; Gambino, J.; Medveczky, P.; Wright, G. E. (1995) J. Med. Chem. 38: 1811–1819.

(38) Argnani, R.; Focher, F.; Zucchini, S.; Verri, A.; Wright, G.; Spadari, S.; Manservigi, R.(1995) Virology. 211, 301–311.

(39) Xu, H.; Maga, G.; Focher, F.; Smith, E. R.; Spadari, S.; Gambino, J.; Wright, G. E. (1995) J. Med. Chem. 38: 49–57.

(36) Klein and Czelusniak, 1990)

(37) Leib, D. A.; Ruffner, K. L.; Hildebrand, C.; Schaffer, P. A., Wright, G. E.; Coen, D. M. (1990) Antimicrob. Agents Chemother. 34: 1285–1286.

(37) Stanberry, 1982)

(38) Gebhardt, B. M.; Wright, G. E.; Xu, H.; Focher, F.; Spadari, S.; Kaufman, H. E. (1996) Antiviral Res., 30:87–94.

(39) Kaufman, H. E.; Varnell, E. D.; Wright, G. E.; Xu, H.; Gebhardt, B. M.; Thompson, H. W. (1996) Antiviral Res. 33: 65–72.

(40) Kokosinski, J; (1979) Organika, 24–30, CA, 94: 65402t

What is claimed is:

1. A compound of formula I wherein:

X is O, $NR_1$, S or $CH_2$;

$R_1$ is hydrogen or $(C_1-C_2)$alkyl;

$R_2$ is hydrogen; $(C_2-C_6)$alkyl optionally substituted by one or more hydroxyl, amino or carboxyl groups, or by phenyl optionally substituted by $(C_1-C_4)$alkyl, carboxyl or amino; $(C_1-C_4)$alkoxy$(C_2-C_6)$alkyl; N—$(C_1-C_4)$alkyl-carboxamido$(C_1-C_2)$alkyl; benzyl in which the phenyl moiety is optionally substituted by $(C_1-C_4)$alkyl, carboxyl or amino; pyrrolyl$(C_1-C_2)$alkyl in which the pyrrole is optionally substituted by $(C_1-C_4)$alkyl; or imidazolyl$(C_1-C_2)$alkyl in which the imidazole is optionally substituted by $(C_1-C_4)$alkyl;

$R_3$ and $R_5$ are the same or different and each is hydrogen; carboxamido; N—$(C_1-C_2)$alkylcarboxamido; carboxamidino; or N—$(C_1-C_2)$alkylcarboxamidino; and $R_4$ is $(C_6-C_{10})$alkyl optionally substituted by one or more hydroxyl, amino, or carboxyl groups; $(C_6-C_{10})$alkyl where the alkyl moiety can form part of a $(C_4-C_8)$ cycloalkyl ring; $(C_6-C_{10})$alkenyl; or $(C_1-C_{14})$alkoxy; or a pharmaceutically acceptable salt thereof, with the proviso that when X is NH, $R_3$ and $R_5$ are hydrogen, and $R_4$ is n-propyl, n-butyl, n-pentyl, i-pentyl, n-hexyl or n-octyl, then $R_2$ is not hydrogen.

2. The compound of claim 1, wherein:

X is O or NH;

$R_2$ is hydrogen; $(C_2-C_6)$alkyl optionally substituted by one or more hydroxyl, amino or carboxyl groups, or by phenyl optionally substituted by $(C_1-C_4)$alkyl, carboxyl or amino; $(C_1-C_4)$alkoxy$(C_2-C_6)$alkyl; benzyl in which the phenyl moiety is optionally substituted by $(C_1-C_4)$alkyl, carboxyl or amino; pyrrolyl$(C_1-C_2)$alkyl in which the pyrrole is optionally substituted by $(C_1-C_4)$alkyl; or imidazolyl$(C_1-C_2)$alkyl in which the imidazole is optionally substituted by $(C_1-C_4)$alkyl;

$R_3$ and $R_5$ are the same or different and each is hydrogen; carboxamido; N—$(C_1-C_2)$alkylcarboxamido; carboxamidino; or N—$(C_1-C_2)$alkylcarboxamidino; and $R_4$ is $(C_6-C_{10})$alkyl optionally substituted by one or more hydroxyl, amino, or carboxyl groups; $(C_6-C_{10})$alkyl where the alkyl moiety can form part of a $(C_4-C_8)$ cycloalkyl ring; $(C_6-C_{10})$alkenyl; or $(C_1-C_{14})$alkoxy.

3. The compound of claim 2, wherein X is NH.

4. The compound of claim 3, wherein:

$R_2$ is $HO(CH_2)_n$, $HO(C=O)(CH_2)_n$, or $H_2N(C_2)_n$, wherein n is 1, 2, 3, 4, or 5;

$R_3$ and $R_5$ are hydrogen; and $R_4$ is $C_8H_{17}$.

5. The compound of claim 4, wherein $R_2$ is $CH_2CH_2OH$, $CH_2CH_2CH_2OH$, $CH_2CH_2NH_2$, or $CH_2CH_2CH_2NH_2$.

6. The compound of claim 3, wherein $R_2$ is $CH_3$, $C_2H_5$, $C_2H_5$, $C_3H_7$, $CH_3OCH_2CH_2$, $CH_3OCH_2CH_2CH_2$, $CH_2C(=O)NHCH_3$, or $CH_2(C=O)NHCH_2CH_3$, and $R_5$ is hydrogen.

7. The compound of claim 3, wherein $R_2$ is $CH_2\emptyset$-$pCH_3$, $CH_2\emptyset$-$pCO_2H$, or $CH_2\emptyset$-$mCO_2H$, wherein the phenyl moiety of said substituents is optionally substituted by $(C_1-C_4)$alkyl, carboxyl or amino, and $R_5$ is hydrogen.

8. The compound of claim 3, wherein $R_2$ is 3-isopropyl-2-pyrrolylmethyl, or midazolylmethyl, and $R_5$ is hydrogen.

9. The compound of claim 3, wherein $R_3$ is $C(=O)NH_2$ or $C(=NH)NH_2$, wherein said $R_3$ substituents are ortho to the carbon atom of the phenyl moiety to which the N atom is attached, and $R_5$ is hydrogen.

10. The compound of claim 3, wherein $R_4$ is $(C_6-C_{10})$ alkyl where the alkyl moiety can form part of a $(C_4-C_8)$ cycloalkyl ring, or $(C_6-C_{10})$alkenyl, and $R_5$ is hydrogen.

11. The compound of claim 10, wherein $R_4$ is trans, trans-CH=CHCH$_2$CH$_2$CH=CHCH$_2$CH$_3$, or CH$_2$-(trans-1-4-cyclohexyl)-CH$_2$CH$_2$CH$_3$.

12. The compound of claim 2, wherein X is O.

13. The compounds 6-(4-octylphenoxy)uracil, 1-methyl-6-(4-hexylanilino)uracil, 1-ethyl-6-(4-hexylanilino)uracil, 1-propyl-6-(4-hexylanilino)uracil, 1-(2-methoxyethyl-6-(4-hexylanilino)uracil, 1-(3-methoxypropyl)-6-(4-hexylanilino)uracil, 1-(2-hydroxyethyl)-6-(4-hexylanilino)uracil, 1-(3-hydroxypropyl)-6-(4-hexylanilino)uracil, 1-(2-methoxyethyl)-6-(4-octylanilino)uracil, 1-(2-hydroxyethyl)-6-(4-octylanilino)uracil, 6-{4-[trans-(4-propylcyclohexyl)methyl]anilino}uracil, 6-[4-trans, trans-octa-1,5-dienyl)anilino]uracil, 1-(N-methylcarboxamidomethyl)-6-(4-octylanilino)uracil, 1-(N-ethylcarboxamidomethyl)-6-(4-octylanilino)uracil, 1-(4-methylbenzyl)-6-(4-octylanilino)uracil, 1-(4-carboxylbenzyl)-6-(4-octylanilino)uracil, 1-(3-carboxylbenzyl)-6-(4-octylanilino)uracil, 1-(4-isopropyl-2-pyrrolylmethyl)-6-(4-octylanilino)uracil, and 1-(4-isopropyl-2-imidazolylmethyl)-6-(4-octylanilino)uracil.

14. A therapeutic composition comprising a therapeutically effective amount of a compound of formula I wherein:

X is O, $NR_1$, S or $CH_2$;

$R_1$ is hydrogen or $(C_1-C_2)$alkyl;

$R_2$ is hydrogen; $(C_2-C_6)$alkyl optionally substituted by one or more hydroxyl, amino or carboxyl groups, or by phenyl optionally substituted by $(C_1-C_4)$alkyl, carboxyl or amino; $(C_1-C_4)$alkoxy$(C_2-C_6)$alkyl; N—$(C_1-C_4)$alkyl-carboxamido$(C_1-C_2)$alkyl; benzyl in which the phenyl moiety is optionally substituted by $(C_1-C_4)$alkyl, carboxyl or amino; pyrrolyl$(C_1-C_2)$alkyl in which the pyrrole is optionally substituted by $(C_1-C_4)$alkyl; or imidazolyl$(C_1-C_2)$alkyl in which the imidazole is optionally substituted by $(C_1-C_4)$alkyl;

$R_3$ and $R_5$ are the same or different and each is hydrogen; carboxamido; N—$(C_1-C_2)$alkylcarboxamido; carboxamidino; or N—$(C_1-C_2)$alkylcarboxamidino; and R₄ is (C₆–C₁₀)alkyl optionally substituted by one or more hydroxyl, amino, or carboxyl groups; (C₆–C₁₀)alkyl where the alkyl moiety can form part of a (C₄–C₈) cycloalkyl ring; (C₆–C₁₀)alkenyl; or (C₁–C₁₄)alkoxy; or a pharmaceutically acceptable salt thereof; and a pharmaceutically acceptable diluent or carrier.

15. The composition of claim 14, wherein in said compound of formula I:

X is O or NH;

R₂ is hydrogen; (C₂–C₆)alkyl optionally substituted by one or more hydroxyl, amino or carboxyl groups, or by phenyl optionally substituted by (C₁–C₄)alkyl, carboxyl or amino; (C₁–C₄)alkoxy(C₂–C₆)alkyl; benzyl in which the phenyl moiety is optionally substituted by (C₁–C₄)alkyl, carboxyl or amino; pyrrolyl(C₁–C₂)alkyl in which the pyrrole is optionally substituted by (C₁–C₄)alkyl; or imidazolyl(C₁–C₂)alkyl in which the imidazole is optionally substituted by (C₁–C₄)alkyl;

R₃ and R₅ are the same or different and each is hydrogen; carboxamido; N—(C₁–C₂)alkylcarboxamido; carboxamidino; or N—(C₁–C₂)alkylcarboxamidino; and

R₄ is (C₆–C₁₀)alkyl optionally substituted by one or more hydroxyl, amino, or carboxyl groups; (C₆–C₁₀)alkyl where the alkyl moiety can form part of a (C₄–C₈) cycloalkyl ring; (C₆–C₁₀)alkenyl; or (C₁–C₁₄)alkoxy.

16. The composition of claim 14, wherein in said compound, X is NH.

17. The composition of claim 14, wherein in said compound, X is O.

18. The composition of claim 14, wherein said compound is 6-(4-octylphenoxy)uracil 1-methyl-6-(4-hexylanilino)uracil, 1-ethyl-6-(4-hexylanilino)uracil, 1-propyl-6-(4-hexylanilino)uracil, 1-(2-methoxyethyl-6-(4-hexylanilino)uracil, 1-(3-methoxypropyl)-6-(4-hexylanilino)uracil, 1-(2-hydroxyethyl)-6-(4-hexylanilino)uracil, 1-(3-hydroxypropyl)-6-(4-hexylanilino)uracil, 1-(2-methoxyethyl)-6-(4-octylanilino)uracil, 1-(2-hydroxyethyl)-6-(4-octylanilino)uracil, 6-{4-[trans-(4-propylcyclohexyl)methyl]anilino}uracil, 6-[4-trans, trans-octa- ,5-dienyl)anilino]uracil, 1-(N-methylcarboxamidomethyl)-6-(4-octylanilino)uracil, 1-(N-ethylcarboxamidomethyl)-6-(4-octylanilino)uracil, 1-(4-methylbenzyl)-6-(4-octylanilino)uracil, 1-(4-carboxylbenzyl)-6-(4-octylanilino)uracil, 1-(3-carboxylbenzyl)-6-(4-octylanilino)uracil, 1-(4-isopropyl-2-pyrrolylmethyl)-6-(4-octylanilino)uracil, and 1-(4-isopropyl-2-imidazolylmethyl)-6-(4-octylanilino)uracil.

19. A method for treating Herpes simplex virus recurrent disease in animals which comprises administering to an animal in need of said treatment an effective amount of a compound of formula I (I)

wherein:

X is O, NR₁, S or CH₂;

R₁ is hydrogen or (C₁–C₂)alkyl;

R₂ is hydrogen; (C₂–C₆)alkyl optionally substituted by one or more hydroxyl, amino or carboxyl groups, or by phenyl optionally substituted by (C₁–C₄)alkyl, carboxyl or amino; (C₁–C₄)alkoxy(C₂–C₆)alkyl; N—(C₁–C₄)alkyl-carboxamido(C₁–C₂)alkyl; benzyl in which the phenyl moiety is optionally substituted by (C₁–C₄)alkyl, carboxyl or amino; pyrrolyl(C₁–C₂)alkyl in which the pyrrole is optionally substituted by (C₁–C₄)alkyl; or imidazolyl(C₁–C₂)alkyl in which the imidazole is optionally substituted by (C₁–C₄)alkyl;

R₃ and R₅ are the same or different and each is hydrogen; carboxamido; N—(C₁–C₂)alkylcarboxamido; carboxamidino; or N—(C₁–C₂)alkylcarboxamidino; and R₄ is (C₆–C₁₀)alkyl optionally substituted by one or more hydroxyl, amino, or carboxyl groups; (C₆–C₁₀)alkyl where the alkyl moiety can form part of a (C₄–C₈) cycloalkyl ring; (C₆–C₁₀)alkenyl; or (C₁–C₁₄)alkoxy; or a pharmaceutically acceptable salt thereof; or a pharmaceutical composition comprising said compound or said salt.

20. The method of claim 19, wherein in said compound of formula I:

X is O or NH;

R₂ is hydrogen; (C₂–C₆)alkyl optionally substituted by one or more hydroxyl, amino or carboxyl groups, or by phenyl optionally substituted by (C₁–C₄)alkyl, carboxyl or amino; (C₁–C₄)alkoxy(C₂–C₆)alkyl; benzyl in which the phenyl moiety is optionally substituted by (C₁–C₄)alkyl, carboxyl or amino; pyrrolyl(C₁–C₂)alkyl in which the pyrrole is optionally substituted by (C₁–C₄)alkyl; or imidazolyl(C₁–C₂)alkyl in which the imidazole is optionally substituted by (C₁–C₄)alkyl;

R₃ and R₅ are the same or different and each is hydrogen; carboxamido; N—(C₁–C₂)alkylcarboxamido; carboxamidino; or N—(C₁–C₂)alkylcarboxamidino; and R₄ is (C₆–C₁₀)alkyl optionally substituted by one or more hydroxyl, amino, or carboxyl groups; (C₆–C₁₀)alkyl where the alkyl moiety can form part of a (C₄–C₈) cycloalkyl ring; (C₆–C₁₀)alkenyl; or (C₁–C₁₄)alkoxy.

21. The method of claim 19, wherein in said compound, X is NH.

22. The method of claim 19, wherein in said compound, X is O.

23. The method of claim 19, wherein said compound is 6-(4-octylphenoxy)uracil, 1-methyl-6-(4-hexylanilino)uracil, 1-ethyl-6-(4-hexylanilino)uracil, 1-propyl-6-(4-hexylanilino)uracil, 1-(2-methoxyethyl-6-(4-hexylanilino)uracil, 1-(3-methoxypropyl)-6-(4-hexylanilino)uracil, 1-(2-hydroxyethyl)-6-(4-hexylanilino)uracil, 1-(3-hydroxypropyl)-6-(4-hexylanilino)uracil, 1-(2-methoxyethyl)-6-(4-octylanilino)uracil, 1-(2-hydroxyethyl)-6-(4-octylanilino)uracil, 6-{4-[trans-(4-propylcyclohexyl)methyl]anilino}uracil, 6-[4-trans, trans-octa-1,5-dienyl)anilino]uracil, 1-(N-methylcarboxamidomethyl)-6-(4-octylanilino)uracil, 1-(N- ethylcarboxamidomethyl)-6-(4-octylanilino)uracil, 1-(4-methylbenzyl)-6-(4-octylanilino)uracil, 1-(4-carboxylbenzyl)-6-(4-octylanilino)uracil, 1-(3-carboxylbenzyl)-6-(4-octylanilino)uracil, 1-(4-isopropyl-2-pyrrolylmethyl)-6-(4-octylanilino)uracil, and 1-(4-isopropyl-2-imidazolylmethyl)-6-(4-octylanilino)uracil.

24. The method of claim 19, wherein said virus is HSV1 or HSV2.

25. The method of claim 24 for treating humans.

26. A method for treating Herpes simplex virus recurrent disease in animals which comprises inhibiting in said animal activity of Herpes simplex virus uracil-DNA glycosylase.

27. The method of claim 26, wherein said virus is HSV1 or HSV2.

28. The method of claim 27 for treating humans.

29. A method for treating Herpes simplex encephalitis in animals which comprises administering to an animal in need of said treatment an effective amount of a compound of formula I wherein:

X is O, $NR_1$, S or $CH_2$;

$R_1$ is hydrogen or $(C_1-C_2)$alkyl;

$R_2$ is hydrogen; $(C_2-_6)$alkyl optionally substituted by one or more hydroxyl, amino or carboxyl groups, or by phenyl optionally substituted by $(C_1-C_4)$alkyl, carboxyl or amino; $(C_1-C_4)$alkoxy$(C_2-C_6)$alkyl; N—$(C_1-C_4)$alkyl-carboxamido$(C_1-C_2)$alkyl; benzyl in which the phenyl moiety is optionally substituted by $(C_1-C_4)$alkyl, carboxyl or amino; pyrrolyl$(C_1-C_2)$alkyl in which the pyrrole is optionally substituted by $(C_1-C_4)$alkyl; or imidazolyl$(C_1-C_2)$alkyl in which the imidazole is optionally substituted by $(C_1-C_4)$alkyl;

$R_3$ and $R_5$ are the same or different and each is hydrogen; carboxamido; N—$(C_1-C_2)$alkylcarboxamido; carboxamidino; or N—$(C_1-C_2)$alkylcarboxamidino; and $R_4$ is $(C_6-C_{10})$alkyl optionally substituted by one or more hydroxyl, amino, or carboxyl groups; $(C_6-C_{10})$alkyl where the alkyl moiety can form part of a $(C_4-C_8)$ cycloalkyl ring; $(C_6-C_{10})$alkenyl; or $(C_1-C_{14})$alkoxy; or a pharmaceutically acceptable salt thereof, or a pharmaceutical composition comprising either said compound or said salt.

30. The method of claim 29, wherein said virus is HSV1 or HSV2.

31. The method of claim 30 for treating humans.

32. A method for treating herpes simplex encephalitis in animals which comprises inhibiting in said animal activity of herpes simplex virus uracil-DNA glycosylase.

33. The method of claim 32, wherein said virus is HSV1 or HSV2.

34. The method of claim 33 for treating humans.

* * * * *